(12) United States Patent
Shaolian et al.

(10) Patent No.: US 7,691,135 B2
(45) Date of Patent: Apr. 6, 2010

(54) SINGLE PUNCTURE BIFURCATION GRAFT DEPLOYMENT SYSTEM

(75) Inventors: Samuel M. Shaolian, Newport Beach, CA (US); Gilbert Madrid, Laguna Niguel, CA (US); To Van Pham, Trabuco Canyon, CA (US); Trinh Van Pham, Stanton, CA (US); Thanh Van Nguyen, Irvine, CA (US)

(73) Assignee: ENDOLOGIX, Inc., Irvine, CA (US)

( * ) Notice: Subject to any disclaimer, the term of this patent is extended or adjusted under 35 U.S.C. 154(b) by 821 days.

(21) Appl. No.: 10/690,227

(22) Filed: Oct. 21, 2003

(65) Prior Publication Data

US 2004/0138735 A1    Jul. 15, 2004

Related U.S. Application Data

(60) Continuation of application No. 09/795,993, filed on Feb. 28, 2001, now Pat. No. 6,663,665, which is a division of application No. 09/266,661, filed on Mar. 11, 1999, now Pat. No. 6,261,316.

(51) Int. Cl.
*A61F 2/06* (2006.01)
*A61F 11/00* (2006.01)

(52) U.S. Cl. ..................... 623/1.11; 606/108

(58) Field of Classification Search ............. 623/1.11, 623/1.12, 1.23, 1.35; 606/108, 194, 195, 606/198
See application file for complete search history.

(56) References Cited

U.S. PATENT DOCUMENTS

| | | | |
|---|---|---|---|
| 5,026,377 A | 6/1991 | Burton et al. | |
| 5,178,634 A | 1/1993 | Martinez | |
| 5,197,976 A | 3/1993 | Herweck et al. | |
| 5,246,452 A | 9/1993 | Sinnott | |
| 5,256,141 A | 10/1993 | Gencheff et al. | |
| 5,275,622 A | 1/1994 | Lazarus et al. | |
| 5,304,200 A | 4/1994 | Spaulding | |
| 5,314,472 A | 5/1994 | Fontaine | |
| 5,316,023 A | 5/1994 | Palmaz et al. | |
| 5,342,387 A | 8/1994 | Summers | |
| 5,360,443 A | 11/1994 | Barone et al. | |
| 5,366,504 A | 11/1994 | Andersen et al. | |

(Continued)

FOREIGN PATENT DOCUMENTS

WO    WO 98/20812 A    5/1998

(Continued)

OTHER PUBLICATIONS

Supplemental European Search Report Application EP 03 79 0040 (The European counterpart of the parent application) mailed on Aug. 21, 2007.

(Continued)

*Primary Examiner*—Vy Q. Bui
(74) *Attorney, Agent, or Firm*—Knobbe Martens Olson & Bear LLP

(57) ABSTRACT

The present invention relates to the endoluminal repair of abdominal aortic aneurysms at the aortic and iliac bifurcation. In particular, a deployment system and graft are disclosed for deploying the bifurcated graft within both iliac branches, as well as the aortic trunk, from a single vascular access.

21 Claims, 19 Drawing Sheets

U.S. PATENT DOCUMENTS

| | | | |
|---|---|---|---|
| 5,370,683 A | 12/1994 | Fontaine | |
| 5,387,235 A | 2/1995 | Chuter | |
| 5,423,886 A | 6/1995 | Arru et al. | |
| 5,425,765 A | 6/1995 | Tiefenbrun et al. | |
| 5,443,498 A | 8/1995 | Fontaine | |
| 5,443,500 A | 8/1995 | Sigwart | |
| 5,456,713 A | 10/1995 | Chuter | |
| 5,489,295 A | 2/1996 | Piplani et al. | |
| 5,496,365 A | 3/1996 | Sgro | |
| 5,507,767 A | 4/1996 | Maeda et al. | |
| 5,522,880 A | 6/1996 | Barone et al. | |
| 5,522,881 A | 6/1996 | Lentz | |
| 5,522,883 A | 6/1996 | Slater et al. | |
| 5,562,726 A | 10/1996 | Chuter | |
| 5,571,172 A | 11/1996 | Chin | |
| 5,571,173 A | 11/1996 | Parodi | |
| 5,578,071 A | 11/1996 | Parodi | |
| 5,591,226 A | 1/1997 | Trerotola et al. | |
| 5,591,228 A | 1/1997 | Edoga | |
| 5,599,305 A | 2/1997 | Hermann et al. | |
| 5,607,445 A | 3/1997 | Summers | |
| 5,628,783 A | 5/1997 | Quiachon et al. | |
| 5,647,857 A | 7/1997 | Anderson et al. | |
| 5,669,924 A | 9/1997 | Shaknovich | |
| 5,676,696 A * | 10/1997 | Marcade | 623/1.35 |
| 5,716,365 A | 2/1998 | Giocoechea et al. | |
| 5,718,724 A | 2/1998 | Giocoechea et al. | |
| 5,720,735 A | 2/1998 | Dorros | |
| 5,733,267 A | 3/1998 | Del Toro | |
| 5,749,880 A | 5/1998 | Banas et al. | |
| 5,755,770 A | 5/1998 | Ravenscroft | |
| 5,769,885 A | 6/1998 | Quiachon et al. | |
| 5,843,160 A | 12/1998 | Rhodes | |
| 5,851,228 A | 12/1998 | Pinheiro | |
| 5,860,998 A | 1/1999 | Robinson et al. | |
| 5,871,536 A | 2/1999 | Lazarus | |
| 5,893,887 A | 4/1999 | Jayaraman | |
| 5,906,640 A | 5/1999 | Penn et al. | |
| 5,916,263 A | 6/1999 | Goicoceha et al. | |
| 5,928,279 A | 7/1999 | Shannon et al. | |
| 5,938,696 A | 8/1999 | Goicoechea et al. | |
| 5,948,018 A | 9/1999 | Dereume et al. | |
| 6,039,749 A | 3/2000 | Marin et al. | |
| 6,039,755 A | 3/2000 | Edwin et al. | |
| 6,039,758 A | 3/2000 | Quiachon et al. | |
| 6,051,020 A | 4/2000 | Goicoechea et al. | |
| 6,070,589 A | 6/2000 | Keith et al. | |
| 6,074,398 A | 6/2000 | Leschinsky | |
| 6,077,296 A | 6/2000 | Shokooji et al. | |
| 6,077,297 A | 6/2000 | Robinson et al. | |
| 6,090,128 A | 7/2000 | Douglas | |
| 6,117,167 A | 9/2000 | Goicoechea et al. | |
| 6,123,722 A | 9/2000 | Fogarty et al. | |
| 6,123,723 A | 9/2000 | Kónya et al. | |
| 6,126,685 A | 10/2000 | Lenker et al. | |
| 6,129,756 A | 10/2000 | Kugler et al. | |
| 6,165,214 A | 12/2000 | Lazarus | |
| 6,168,610 B1 | 1/2001 | Marin et al. | |
| 6,187,036 B1 | 2/2001 | Shaolian et al. | |
| 6,192,944 B1 | 2/2001 | Greenhalgh | |
| 6,197,049 B1 | 3/2001 | Shaolian et al. | |
| 6,261,316 B1 | 7/2001 | Shaolian et al. | |
| 6,352,561 B1 | 3/2002 | Leopold et al. | |
| 6,355,060 B1 | 3/2002 | Lenker et al. | |
| 2006/0100686 A1 | 5/2006 | Bolduc et al. | |

FOREIGN PATENT DOCUMENTS

| | | |
|---|---|---|
| WO | WO 00/53251 A | 9/2000 |
| WO | WO 01/03762 A | 1/2001 |
| WO | WO 02/060345 A | 8/2002 |
| WO | WO 2005/037076 | 4/2005 |

OTHER PUBLICATIONS

Patent Cooperation Treaty (PCT) International Search Report, International Application No. PCT/US2007/078565, Filed on Sep. 14, 2007, in 7 pages.

* cited by examiner

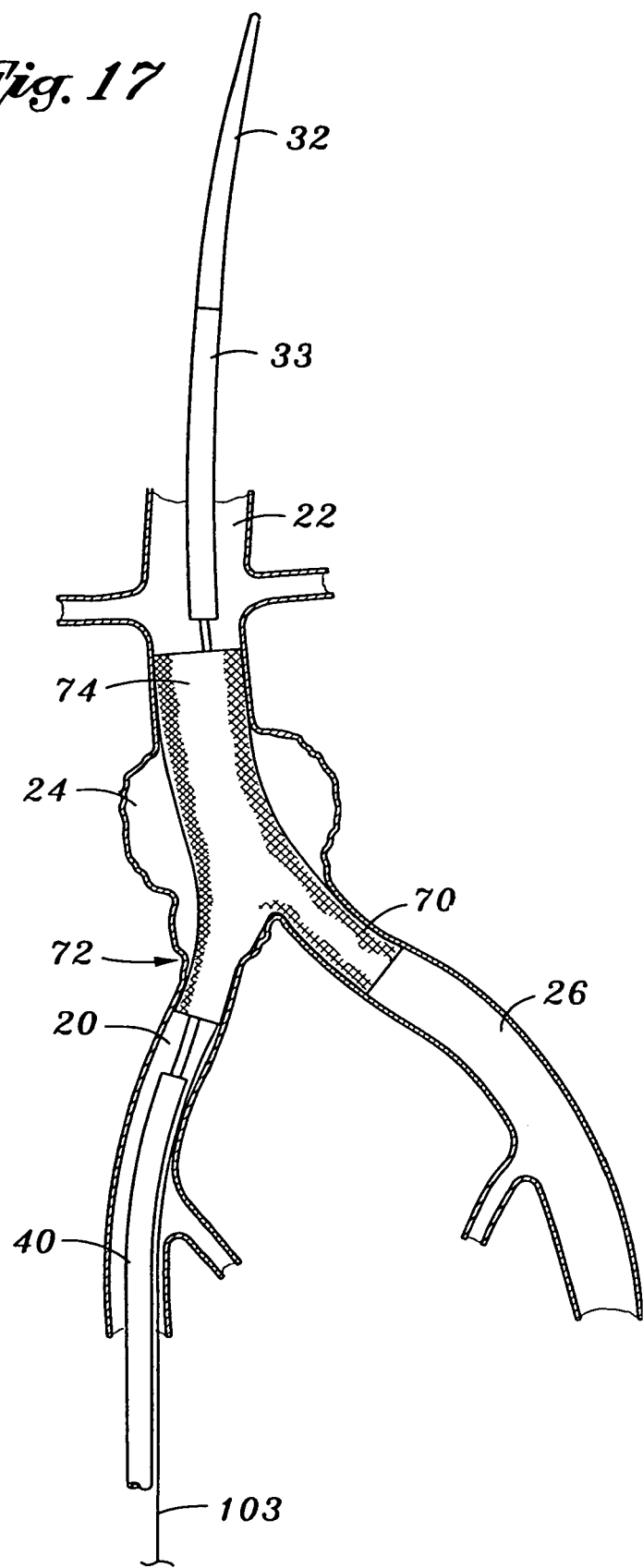

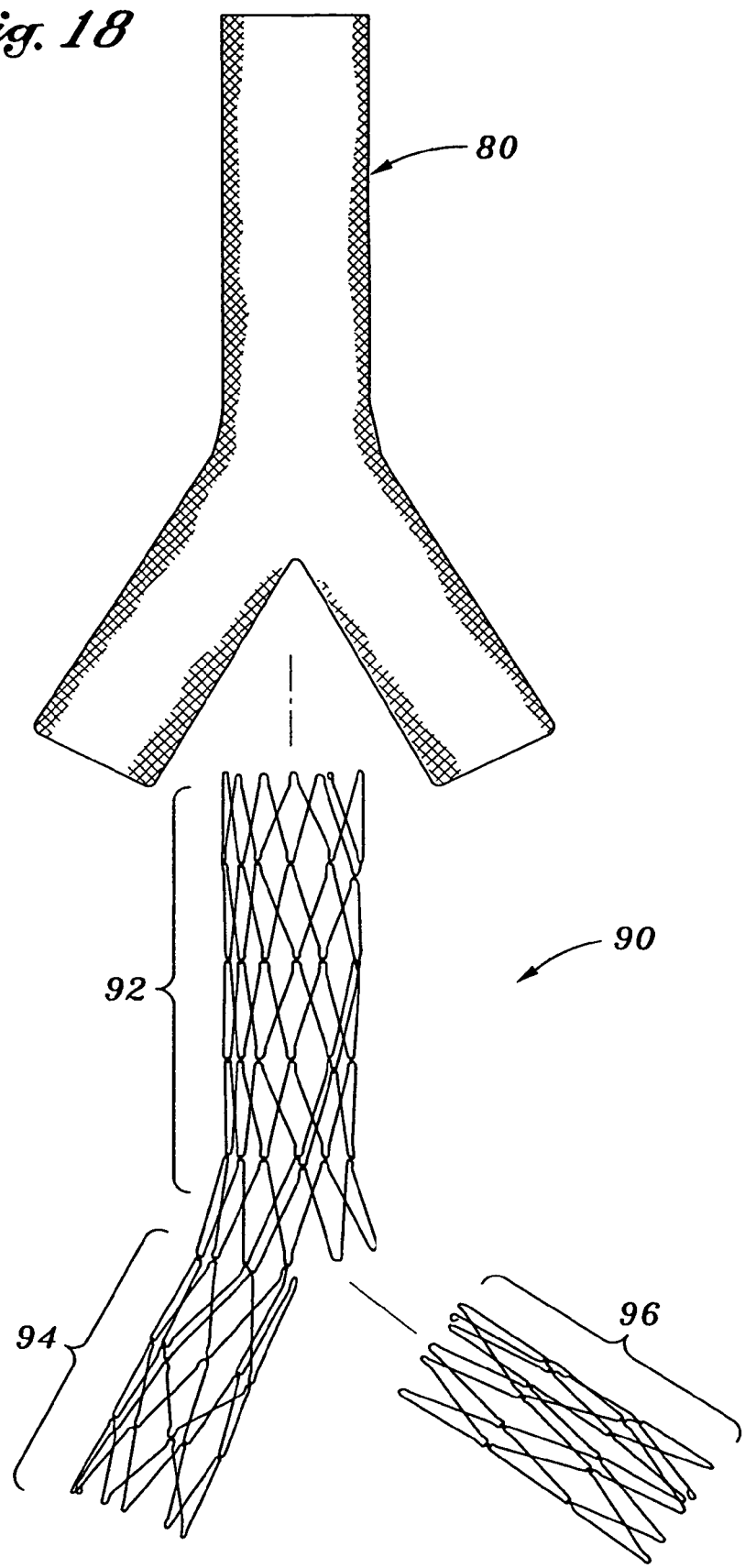

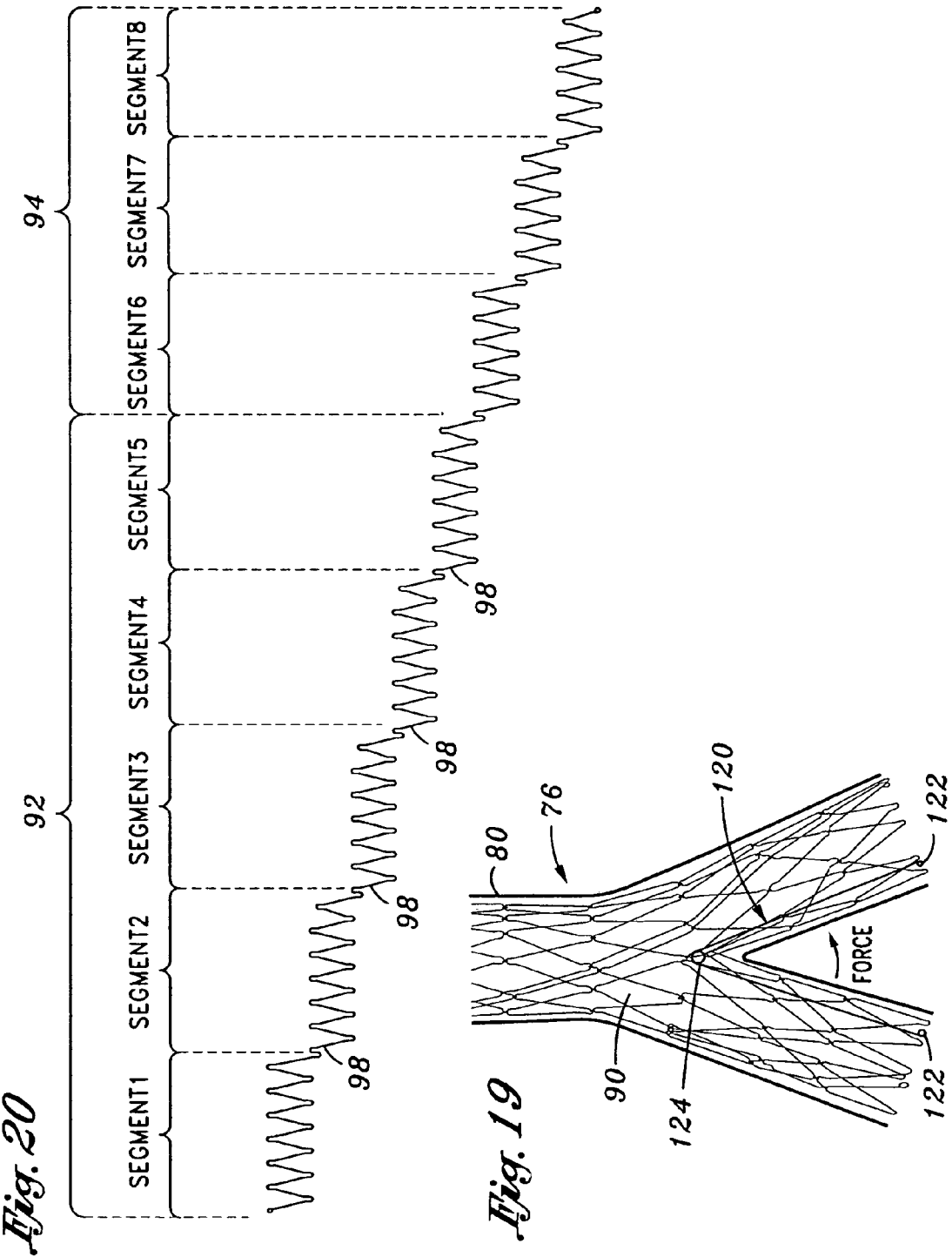

SINGLE PUNCTURE BIFURCATION GRAFT DEPLOYMENT SYSTEM

RELATED APPLICATIONS

This application is a continuation of U.S. patent application Ser. No. 09/795,993, filed Feb. 28, 2001, now U.S. Pat. No. 6,663,665, which is a divisional of U.S. patent application Ser. No. 09/266,661 filed on Mar. 11, 1999, now U.S. Pat. No. 6,261,316.

BACKGROUND OF THE INVENTION

The present invention relates to the endoluminal repair of abdominal aortic aneurysms at the aortic and iliac bifurcation, and more particularly, to a deployment system used to deploy a self-expanding prosthesis.

Endoluminal repair or exclusion of aortic aneurysms has been performed for the past several years. The goal of endoluminal aortic aneurysm exclusion has been to correct this life threatening disease in a minimally invasive manner in order to effectuate a patient's quick and complete recovery. Various vascular grafts exist in the prior art that have been used to exclude aortic aneurysms. These prior art grafts have met varying degrees of success.

Initially, straight tube grafts were used in the infrarenal abdominal aorta to exclude the aneurysmal sac from the blood stream thereby resulting in the weakened aortic wall being protected by the graft material. These straight tube grafts were at first unsupported, meaning that they employed stents at their proximal and distal ends to anchor the proximal and distal ends of the graft to the healthy portions of the aorta, thereby leaving a midsection of the graft or prosthesis that did not have any internal support. Although this type of graft at first appeared to correct the aortic aneurysm, it met with many failures. The unsupported nature of its midsection allowed the graft to migrate distally as well as exhibit significant proximal leakage due to the enlargement of the aorta without adaptation of the graft, such as enlargement of the graft, to accommodate the change in diameter of the aorta.

Later, technical improvements in stent design led to "self-expanding" stents. In addition, later improvements produced "Nitinol" stents that had a "memory" that was capable of expanding to a predetermined size. Coincidentally, graft designers began to develop bifurcated grafts having limbs that extended into the iliac arteries. The development of bifurcated grafts allowed for the treatment of more complex aneurysms. With the advent of bifurcated grafts, the need for at least a 1.0 cm neck from the distal aspect of the aneurysmal sac to the iliac bifurcation in order to treat the aneurysm with an endoluminal graft was no longer needed. However, proximal necks of at least 0.5 to 1.0 cm distance from the renal arteries to the most proximal aspect of the aneurysm are still generally required.

Some bifurcated grafts are of a two-piece design, in which an aorta and ipsilateral iliac segment is connected with a contralateral iliac branch in situ. The two-piece designs require the insertion of a contralateral limb through a separate access site. These types of grafts are complex to deploy and have the potential for leakage at the connection site of the two limbs of the graft.

One-piece bifurcated grafts are also known in the art. For example, U.S. Pat. No. 2,845,959 discloses a one-piece seamless woven textile bifurcated tube for use as an artificial artery. Yarns of varying materials can be used to weave the bifurcated graft including nylon and plastic yarns. U.S. Pat. Nos. 3,096,560 and 3,029,9819 issued to Liebig and Starks, respectively, disclose woven one-piece bifurcated grafts which are constructed by performing specific types of winding and weaving about a smooth bifurcated mandrel.

U.S. Pat. No. 4,497,074 describes a one-piece bifurcated graft that is made from a preformed support in the shape of the bifurcated graft. In a first stage, a gel enabling a surface state close to that of the liquid-air interface to be obtained at the gel-air interface is deposited by dipping or coating the preform with a sol which is allowed to cool. A hardenable flexible material such as a silicone elastomer is applied by dipping or spraying the material on the mold in a second stage. Finally, after hardening of the material, the prosthesis is removed from the mold. In U.S. Pat. No. 4,816,028 issued to Kapadia et al., there is shown a one-piece woven bifurcated vascular graft having a plurality of warp threads running in the axial direction and a plurality of weft threads running in the transverse direction. Further, U.S. Pat. No. 5,108,424 issued to Hoffman, Jr. et al. discloses a one-piece bifurcated collagen-impregnated Dacron graft. The bifurcated graft includes a porous synthetic vascular graft substrate formed by knitting or weaving with at least three applications of dispersed collagen fibrils.

The Herweck et al. patent, U.S. Pat. No. 5,197,976, discloses a continuous one-piece bifurcated graft having plural longitudinally parallel tube structures which are attached to one another over at least a portion of their longitudinal exteriors. The tube structures can be manually separated to form a branched tubular structure. The prosthesis is manufactured by paste forming and stretching and/or expanding highly crystalline unsintered polytetrafluoroethylene (PTFE). Paste forming includes mixing the PTFE resin with a lubricant, such as mineral spirits, and then forming the resin by extrusion into shaped articles.

Although all of the above-described one-piece bifurcated grafts have eliminated the problems of leakage and graft failure at the suture or juncture site associated with two piece bifurcated grafts which join together two separate grafts to form the bifurcated graft, problems still exist with these one-piece bifurcated grafts. For example, the previously described one-piece bifurcated grafts do not include an integral support structure to prevent the deformation, twisting or collapse of the graft limbs. Further, the same problems with graft migration that existed with straight tube grafts still exist with the one-piece bifurcated grafts. Accordingly, there is a need for a stable and durable transluminally implantable bifurcated vascular graft that is structured to prevent the migration and deformation of the graft and obstruction of the blood flow through the limbs of the bifurcated graft.

Endoluminal implantation is an increasingly accepted technique for implanting vascular grafts. Typically, this procedure involves percutaneously inserting a vascular graft or prosthesis by using a delivery catheter. This process eliminates the need for major surgical intervention thereby decreasing the risks associated with vascular and arterial surgery. Various catheter delivery systems for prosthetic devices are described in the prior art.

For example, bifurcated vascular grafts have been created by combining grafts with stents on delivery systems in order to secure the graft ends to the blood vessel thereby stabilizing the bifurcated graft. In U.S. Pat. No. 5,360,443 issued to Barone et al., a method for repairing an abdominal aortic aneurysm is described. The method comprises the steps of (1) connecting an expandable and deformable tubular member, such as a stent, to each of the tubular passageways of a bifurcated graft, (2) disposing the bifurcated graft and deformable tubular members within the aortic and iliac arteries, and (3) expanding and deforming each deformable tubular member with a catheter to secure each tubular passageway of the bifurcated graft within the appropriate artery. This reference only discloses a catheter delivery method for deploying the aortic portion of the bifurcated graft. The same catheter is supposedly used to also expand and secure the associated stents within the iliac arteries.

The Palmaz et al. patent, U.S. Pat. No. 5,316,023, describes a method and apparatus for repairing an abdominal aortic aneurysm in an aorta at the iliac arteries. This method includes the steps of connecting a first tubular graft to a first deformable and expandable tubular member, connecting a second tubular graft to a second deformable and expandable tubular member, disposing the first tubular graft and first tubular member upon a first catheter having an inflatable portion, disposing the second tubular graft and second tubular member upon a second catheter having an inflatable portion, intraluminally delivering the first and second tubular grafts, tubular members and catheters to the aorta and disposing at least a portion of each tubular graft within the abdominal aortic aneurysm, and expanding the tubular members with the inflatable catheters to secure them and at least a portion of their associated tubular grafts within the aorta. This patent reference employs two separate unconnected straight grafts that are employed within an aorta to form a bifurcated graft.

Further, U.S. Pat. No. 4,617,932 issued to Kornberg discloses a device for inserting a graft into an artery comprising a plurality of nested tubes each having an upper and lower end. A first outer tube has a means for guiding and positioning an arm means at its upper end. The arm means is movably attached to the upper end of another tube located inside of the first tube and extending above the first outer tube. The lower ends of the tubes are adaptable for fastening means and the inside tube extends below the end of the first outer tube. Delivery and placement of a bifurcated graft is illustrated. U.S. Pat. No. 5,522,883 issued to Slater et al. describes an endoprosthesis stent/graft deployment system which includes a tubular delivery catheter, a radially expandable prosthesis positioned over the catheter, a removable endoprosthesis support assembly located adjacent the catheter opening and having an arm extending through the catheter which keeps the endoprosthesis in a compressed state, and a release mechanism insertable through the catheter for removing the support assembly.

U.S. Pat. No. 5,104,399 issued to Lazarus also describes an artificial graft and delivery method. The delivery system includes a capsule for transporting the graft through the blood vessel, a tube connected to the vessel that extends exterior to the vessel for manipulation by a user, and a balloon catheter positioned within the tube. Finally, U.S. Pat. No. 5,489,295 issued to Piplani et al. discloses a bifurcated graft and a method and apparatus for deploying the bifurcated graft. The Piplani et al. graft includes a main tubular body, first and second tubular legs joined to the main tubular body in a bifurcation, a first expandable attachment means for anchoring the main body located adjacent the opening for the first body, and a second expandably attachment means located adjacent the opening of the first tubular leg for anchoring the first tubular leg. The graft is intraluminally implanted using a catheter that is inserted into the aortic bifurcation through a first iliac artery so that the first attachment means adjacent the opening of the main body can be anchored in the aorta and the second attachment means adjacent the opening of the first tubular; leg can be anchored in the first iliac artery. The second tubular leg is deployed into the second iliac artery by using a pull line attached to the second tubular leg. The Piplani et al. patent also discloses a deployment device consisting of a capsule catheter, a balloon catheter, and a separate expandable spring attachment means.

None of the described methods and devices permits delivery of a one-piece bifurcated graft from a single access site. Indeed, current procedures require a double or triple cutdown or percutaneous access to the left and right femoral and/or brachial arteries to insert catheters, guidewires, and guide catheters. Accordingly, not only is there a need, for an improved structurally supported self expandable one piece bifurcated graft, but there is also a need for a delivery apparatus and method for deploying and implanting such a bifurcated graft from a single access site.

SUMMARY OF THE INVENTION

There is disclosed in accordance with the present invention a deployment system for deploying a bifurcated prosthesis at the junction of a main vessel and first and second branch vessels. The system comprises a delivery catheter and a bifurcated prosthesis. The delivery catheter has an inner core connected to a tubular housing and slidably positioned within a middle core. The middle core has proximal and distal ends and at least the distal end of the middle core forms a tubular sheath. The middle core is slidably positioned within an outer sheath. The bifurcated prosthesis in accordance with the deployment system of the present invention has a main body section with proximal and distal ends and first and second branch sections at the proximal end of the main body section. The main body section is held in a radially compressed state within the tubular housing of the inner core. The first branch section is held in a radially compressed state within the tubular sheath of the middle core. And the second branch section is disposed within the outer sheath in a radially compressed state.

A method is disclosed for deploying bifurcated endoluminal prosthesis at the junction of a main vessel, such as the aorta, and first and second branch vessels, such as the ipsilateral and contralateral iliac arteries. A deployment system is introduced through an access site into the first branch vessel and advanced distally (catheter direction) through at, least a portion of the first branch vessel and into the main vessel. The deployment system contains a bifurcated prosthesis comprising a main body section and first and second branch sections. The proximal end of the second branch section is extended outward from the deployment system into the main vessel in the direction of the second branch vessel by proximally retracting an outer sheath of the deployment system. The extended second branch section is positioned within the second branch vessel by proximally retracting the deployment system.

The first branch section of the prosthesis is expanded from a radially compressed state within the deployment system to a radially expanded state within the first branch vessel by proximally retracting a middle core of the deployment system. The main body section of the prosthesis is expanded from a radially compressed state within the deployment system to a radially expanded state within the main vessel by distally advancing an inner core of the deployment system. The second branch section within the second branch vessel is expanded and the deployment system is retracted distally through a central lumen in the main body and first branch sections of the prosthesis and out of the patient's body.

In one embodiment of the disclosed method, the second branch section comprises a wire support formed from a memory alloy. Consequently, the second branch section may be expanded by heating the wire support.

Alternatively, the second branch section may comprise a self-expandable wire support, which is mechanically restrained in a radially compressed state by a restraint. The second branch section is then expanded by removing the restraint. The restraint may comprise any of a variety of structures, such as a wire woven through or around the collapsed second branch or a sheath around the collapsed second branch. In one embodiment, the sheath is peelable or tearable so that it can be removed by retraction in the proximal catheter direction. The second branch section is expanded by axially moving the wire or sheath.

Further features and advantages of the present invention will become apparent to those of skill in the art in view of the disclosure herein, when considered together with the attached drawings and claims.

BRIEF DESCRIPTION OF THE DRAWINGS

FIG. 17 is a representation of the system as in FIG. 16, with the ipsilateral limb deployed.

FIG. 18 is an exploded view of a bifurcated graft in accordance with the present invention, showing a self expandable wire cage separated from an outer polymeric sleeve.

FIG. 19 is schematic representation of the bifurcated graft in accordance with one embodiment of the present invention, showing an expansion spring.

FIG. 20 is plan view of a formed wire useful for rolling into a multi-segmented wire cage in accordance with the present invention.

DETAILED DESCRIPTION OF THE PREFERRED EMBODIMENT

This invention relates to a delivery catheter and graft system for deploying a bifurcated vascular graft, which allows deployment of the graft from a single vascular access site. A related technique using two access sites is disclosed in co-pending patent application Ser. No. 08/802,478 entitled Bifurcated Vascular Graft and Method and Apparatus for Deploying Same, filed Feb. 20, 1997, the disclosure of which is incorporated in its entirety herein by reference.

Figure 1:
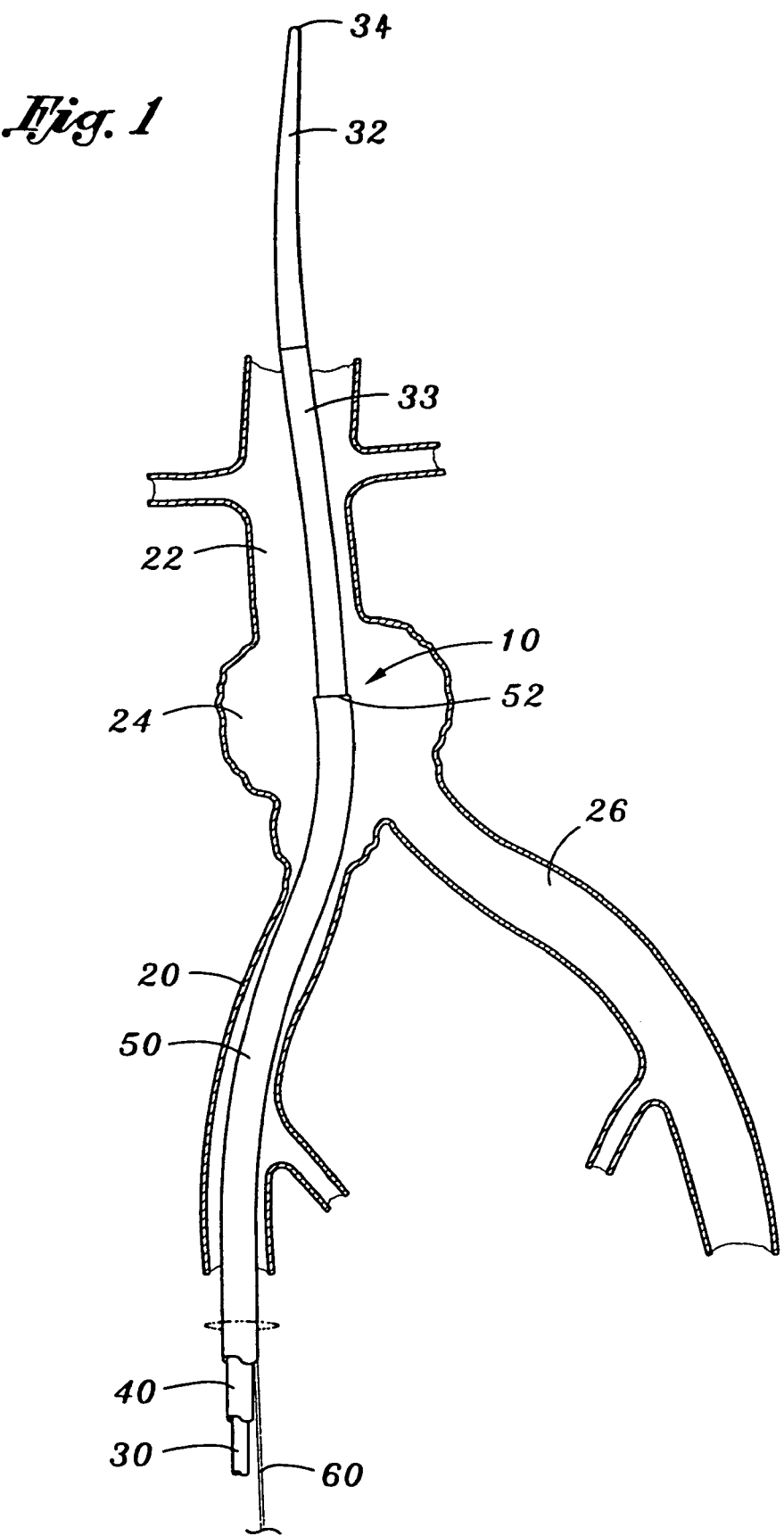
FIG. 1 is a schematic representation of the deployment system of the present invention positioned within the ipsilateral iliac and the aorta.

Referring to FIG. 1, an embodiment of the deployment system 10 is depicted in situ at the bifurcation of the aorta into the ipsilateral iliac 20 (in which the deployment system 10 resides) and the contralateral iliac 26. In general, the illustrated deployment system 10 employs an over-the-wire coaxial design with three inter-moving elements and, in one embodiment, a thermal or electrical conduit as will be described. The deployment system 10 is percutaneously (or surgically) inserted into a first access site such as a femoral artery puncture (not illustrated). The system 10 is advanced distally along a guidewire through the ipsilateral iliac 20 and into the aorta 22, until positioned as generally illustrated in FIG. 1, spanning the site of an aortic aneurysm 24.

In an embodiment intended for femoral artery access to deploy an abdominal aortic aneurysm bifurcation graft, the deployment system 10 has an overall length from proximal to distal end generally within the range of from about 90 cm to about 110 cm. As used herein, the relative terms "proximal" and "distal" shall be defined from the perspective of the delivery system 10. Thus, proximal is in the direction of the control end of the system (not illustrated) and distal is in the direction of the distal tip 32.

The illustrated deployment system 10 includes an inner core 30, a middle core 40, an outer sheath 50, and a contralateral graft actuator 60. The inner core 30 is preferably a thin-walled tube designed to track over a guidewire, such as a standard 0.035 inch guidewire. In the illustrated embodiment, the inner core 30 preferably has as small an outside diameter as possible to minimize the overall outside diameter of the delivery catheter, while at the same time providing sufficient column strength to permit distal axial advancement of the tapered tip 32 and tubular housing 33 to deploy the main trunk of the prosthesis as will be discussed. A section of stainless steel hypotube having an inside diameter of about 0.042 inches, an outside diameter of about 0.058 inches, and an overall length of about 95 cm, depending upon the length of the delivery catheter, has been found suitable for this purpose.

The device 10 has a soft tapered tip 32 secured to the distal end of inner core 30. Tapered tip 32 facilitates insertion and atraumatic navigation of the vasculature. The tapered tip 32 can be made from any of a variety of polymeric materials well known in the medical device arts, such as polyethylene, nylon, PTFE, and PEBAX.

The distal tapered tip 32 tapers in one embodiment from an outside diameter of about 0.225 inches at its proximal end to an outside diameter of about 0.070 inch at its distal end. The overall length of the distal tip 32 in one embodiment of the deployment system 10 is about 3 inches. However, the length and rate of taper of the distal tip 32 can be varied within the range of from about ½ inch to about 4 or 5 inches, depending upon the desired tractability and flexibility characteristics.

A tubular housing 33 extends proximally from and is attached to or is a proximal extension of the distal tip 32. The tubular housing 33 and distal tip 32 are connected to the inner core 30, so that distal advancement of the inner core 30 will also distally advance the tip 32 and housing 33. The tubular housing 33 serves as a sheath for retaining the compressed main body of the bifurcated graft of the present invention. In one embodiment, the tubular housing 33 comprises a polyolefin extrusion having a length of about 15 cm an inside diameter of about 0.2-10 inches and an outside diameter of about 0.225 inches.

The distal end of the tubular housing 33 is secured to the proximal end of the distal tip 32 such as by heat shrinking, thermal bonding, adhesive bonding, and/or any of a variety of other securing techniques known in the art. Alternatively, the tip 32 and housing 33 may be integrally formed such as by extrusion followed by heated stretching or other technique to taper the distal end. The distal tip 32 is preferably also directly or indirectly connected to the inner core 30 such as by a friction fit, adhesives or thermal bonding.

The middle core 40 comprises an elongate flexible tubular body adapted to axially slidably track over the inner core 30. In the illustrated embodiment, the middle core 40 comprises a polyethylene or PTFE extrusion having an inside diameter of about 0.180 inches and an outside diameter of about 0.220 inches. The inner and/or outer surfaces of the middle core 40 may be further provided with a lubricious coating such as paralene, silicone, PTFE or others well known in the art.

Figure 3:
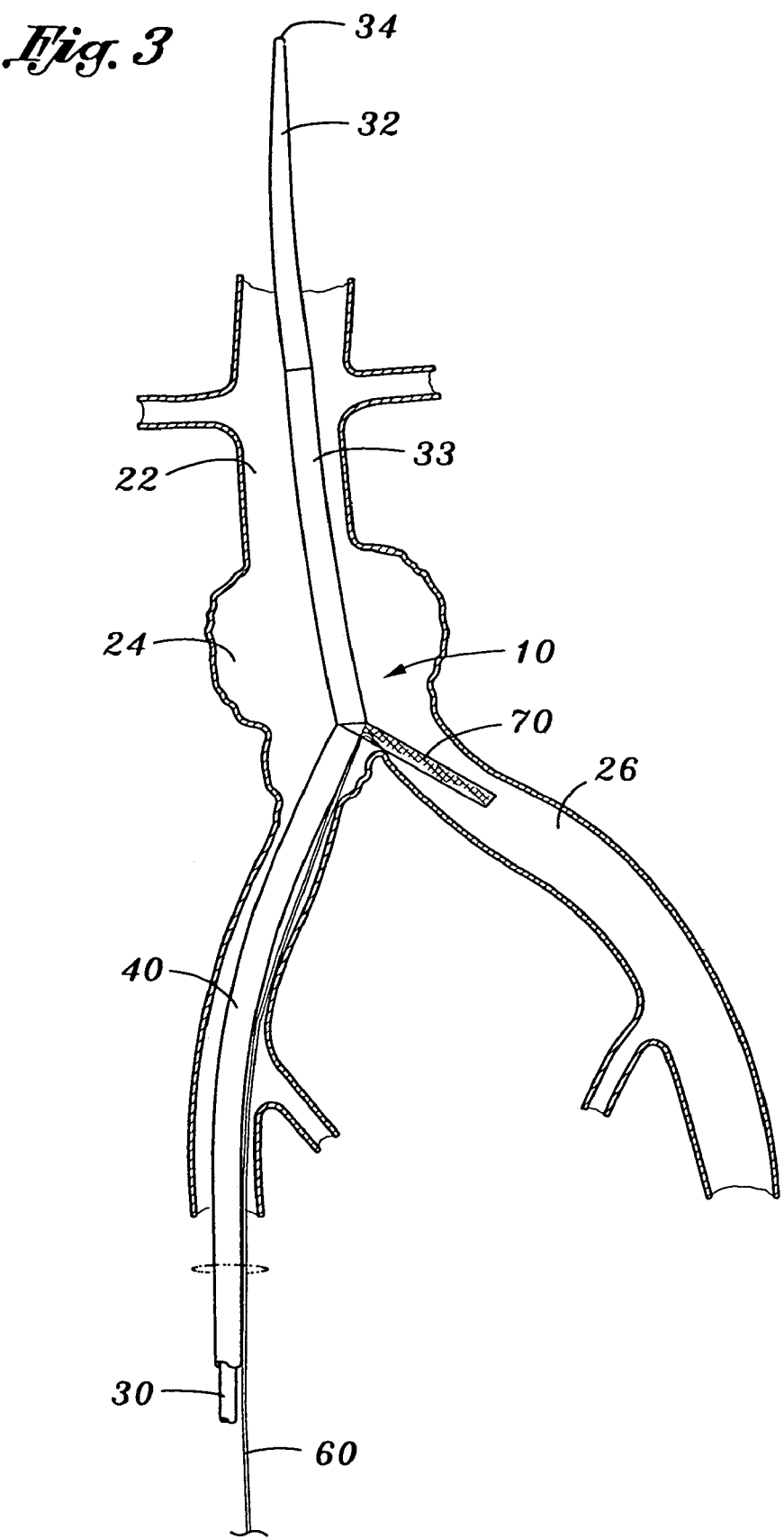
FIG. 3 is a schematic representation of the deployment system of the present invention illustrating positioning of the ipsilateral and contralateral limbs of the bifurcated graft within the respective iliac branches by proximal retraction of the deployment catheter.

The middle core 40 has a tubular distal end to slidably receive ipsilateral iliac limb 72 of the graft as will be discussed (See, e.g., FIGS. 3 and 4). The middle core 40 may be tubular throughout its length, or may comprise a pull wire or ribbon throughout a proximal portion thereof (See, e.g., FIG. 5). The tubular distal segment has an axial length of at least about 5 cm or longer depending upon the dimensions of the graft.

The outer core 50 comprises an elongate, flexible tubular body, slidably positioned over the middle core 40. Outer core 50 also entraps the restrained contralateral limb against the outside surface of middle core 40 in the illustrated embodiment.

In one embodiment, the outer sheath 50 comprises extruded PTFE, having an outside diameter of about 0.250 inches and an inside diameter of about 0.230 inches. The outer sheath 50 has an axial length within the range of from about 40 inches to about 55 inches. In the loaded configuration illustrated in FIG. 1, the distal end 52 of the outer sheath 50 is located at least about 6 cm proximally of the distal end 34 of the tapered tip 32. The outer sheath 50 may be provided at its proximal end (not shown) with a manifold having a hemostatic valve and access ports, such as for the infusion of drugs or contrast media as will be understood by those of skill in the art.

Figure 2:
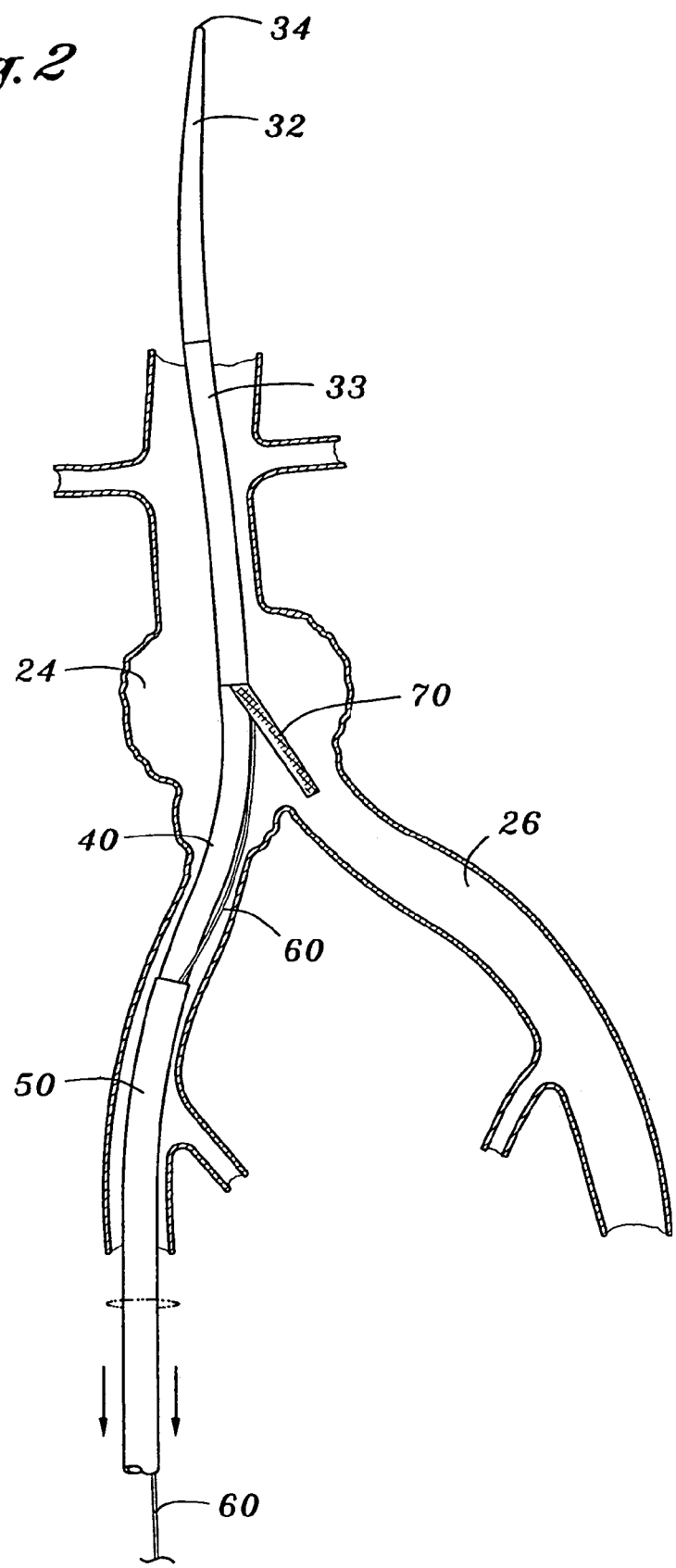
FIG. 2 is a schematic representation of the deployment system of the present invention positioned within the ipsilateral iliac and the aorta, showing separation of the contralateral limb from the ipsilateral limb.

With reference to FIG. 2, as the outer sheath 50 is retracted proximally, the contralateral limb 70 separates from the middle core 40 and inclines laterally due to the resilience of the wire cage in the contralateral limb 70. Alternatively, the limbs may separate due to an internal separation spring connected to the ipsilateral and contralateral limbs, with the apex of the spring located at the bifurcation. See, e.g., FIG. 14) The ipsilateral limb (hidden) remains sheathed by the middle core 40. The main body of the stent graft remains sheathed by the tubular housing 33.

Figure 4:
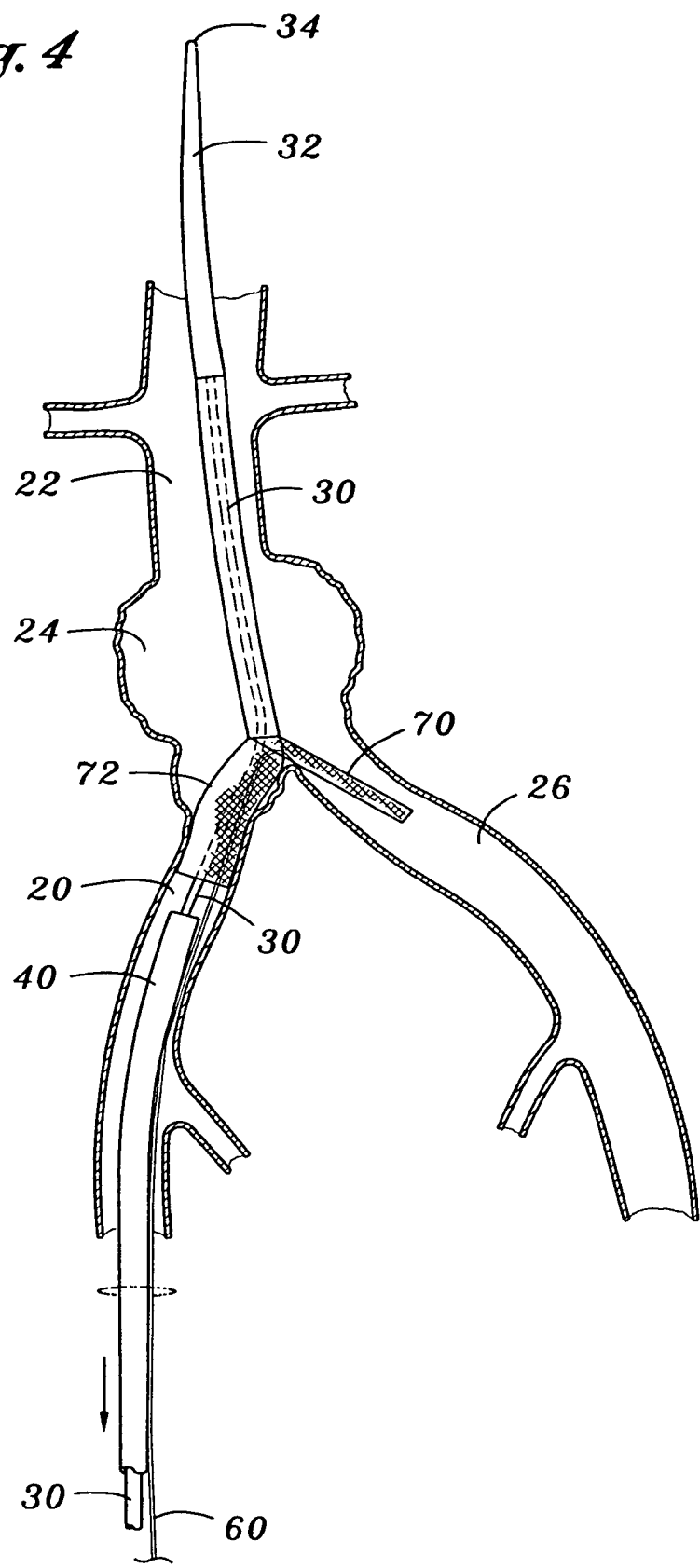
FIG. 4 is a schematic representation of the deployment system of the present invention showing deployment of the ipsilateral limb of the bifurcated graft by withdrawal of the middle core.

The self-expandable ipsilateral limb 72 of the graft is deployed within the ipsilateral iliac 20, as illustrated in FIG. 4, by proximally retracting the middle core 40. In the embodiment shown in FIG. 4, the middle core 40 comprises a thin-walled length of PTFE tubing having an outside diameter of about 0.215 inches. The middle core 40 moves axially with respect to the inner core 30.

Figure 5:
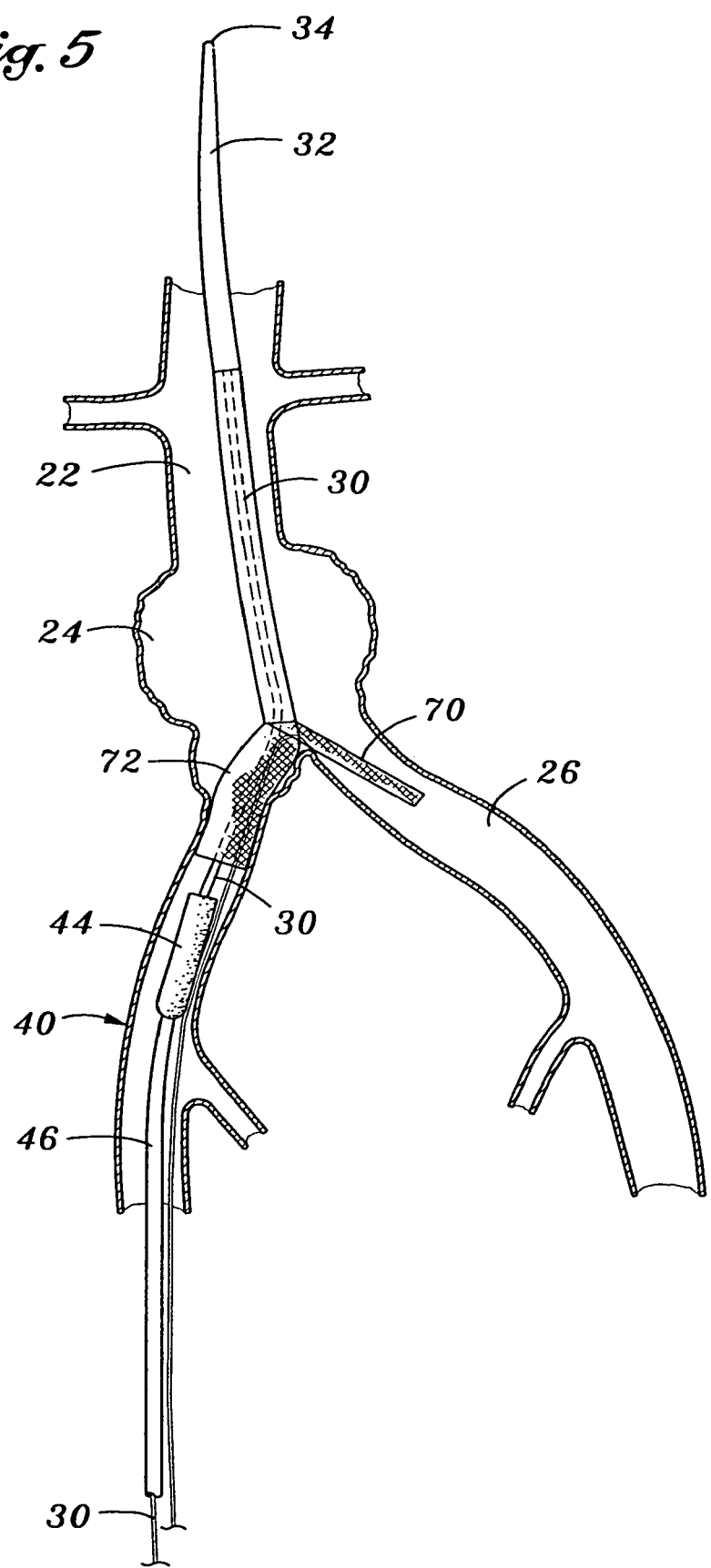
FIG. 5 is a schematic representation of the deployment system of the present invention showing a segmented configuration of the middle core.

Referring to FIG. 5, a variation of the middle core 40 design consists of a relatively short ipsilateral sheath section 44, which is necked down such as by heat shrinking to secure the ipsilateral sheath section 44 to a longer tubular extension 46, the combination forming the modified middle core 40. As described above, the ipsilateral limb 72 of the graft is deployed by proximally withdrawing the tubular extension 46 so that retraction of the ipsilateral sheath section 44 releases the self-expandable wire cage from its compressed state in the ipsilateral limb 72. The length of sheath 44 is generally in the range of from about 5 cm to about 9 cm. In one embodiment in which the ipsilateral limb 72 has a length of about 5.5 cm, the sheath 44 has a length of about 5.5 cm.

Figure 6:
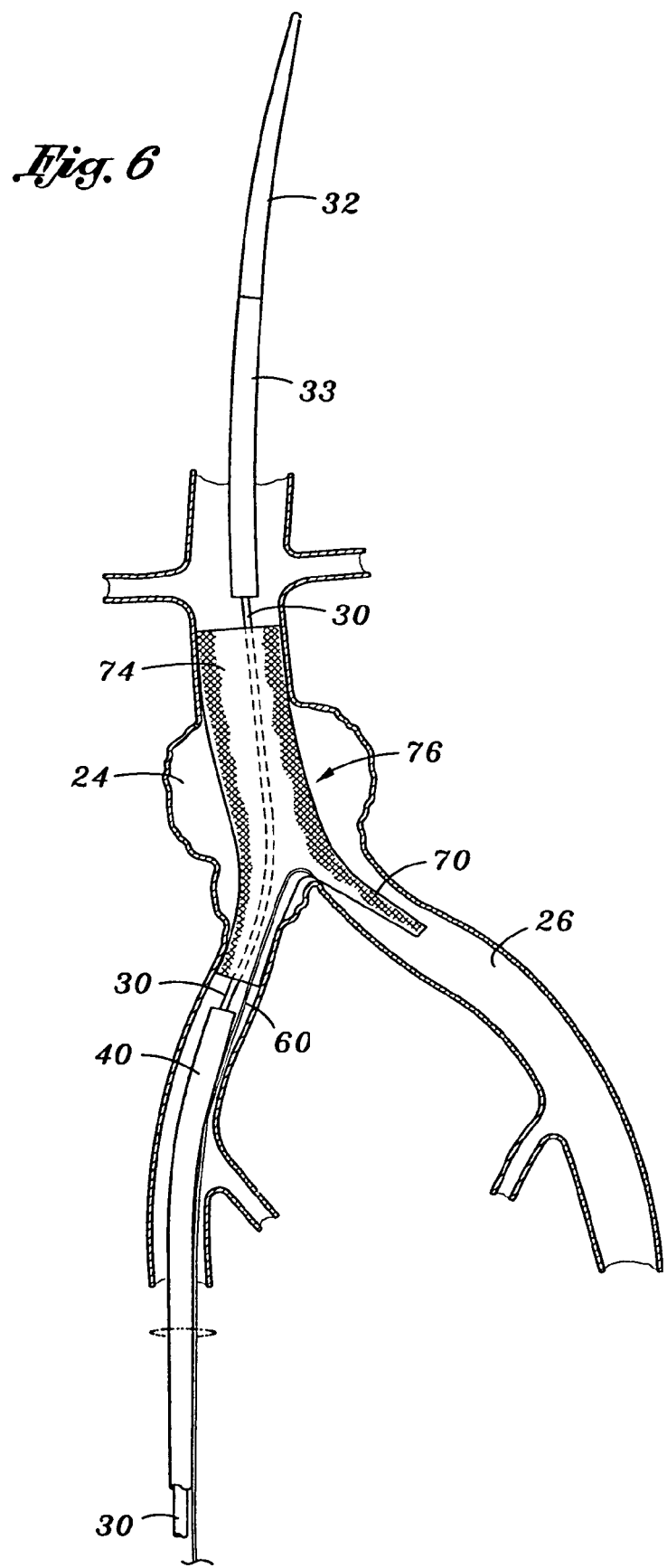
FIG. 6 is a schematic representation of the deployment system of the present invention showing deployment of the main body of the bifurcated graft by distally advancing the inner core.

Referring to FIG. 6, the self-expanding aortic trunk portion, or main body 74 of the graft 76 is released from its compressed state within the tubular housing 33 by distally advancing the inner core 30. Because the tubular housing 33 and distal tip 32 are attached to the inner core 30, the distal movement of the inner core causes the housing 33 to advance, thereby permitting the main body 74 of the graft to expand to its larger, deployed diameter.

Figure 7:
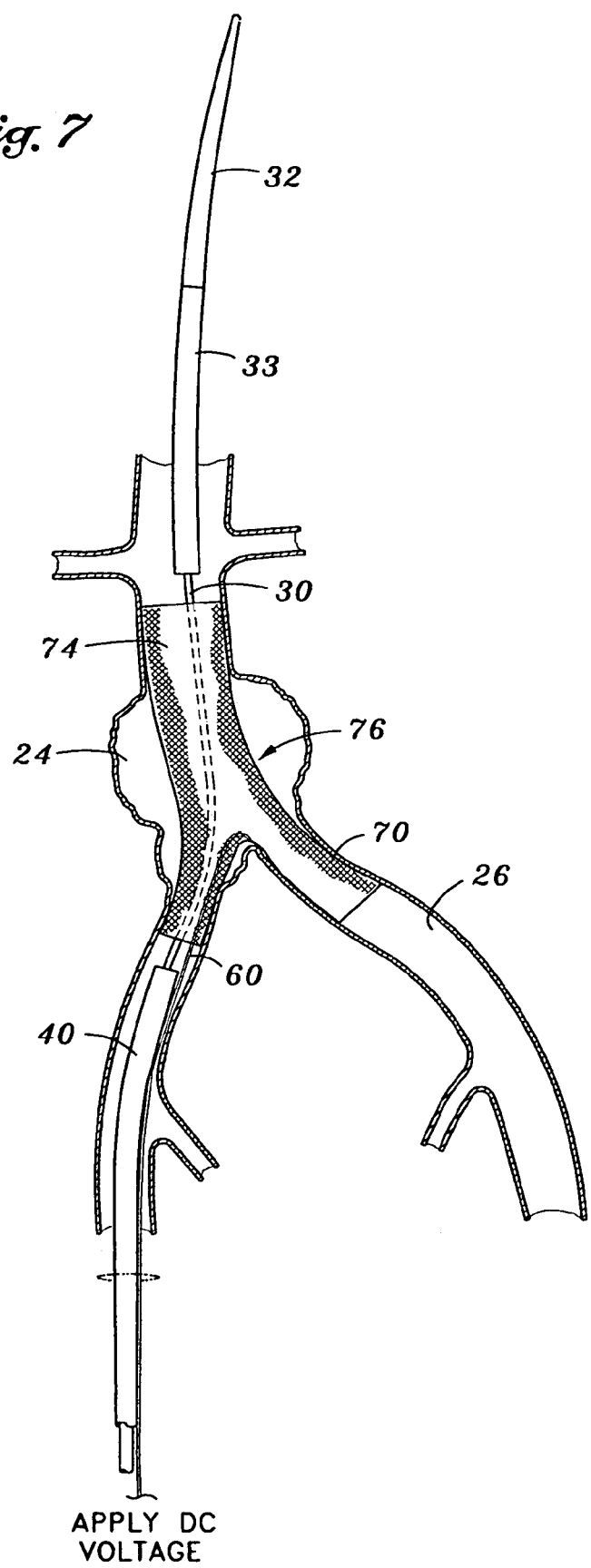
FIG. 7 is a schematic representation of the deployment system of the present invention illustrating deployment of the contralateral limb of the bifurcated graft by applying heat, in the illustrated embodiment to the memory alloy wire cage of the contralateral limb.

As illustrated in FIG. 7, the contralateral limb 70 of the graft 76 may then be expanded within the contralateral iliac 26 by activation of the contralateral graft actuator 60. In an embodiment in which the contralateral graft comprises a memory metal, expansion may be accomplished by heating the contralateral limb via actuator 60. When the memory alloy support within the contralateral limb 70 reaches its transition temperature, which may be between 40-60° C. for Nitinol, the compressed wire expands to its predetermined tubular shape.

In one embodiment, power from a DC power supply or RF generator is transferred to the wire support cage from the proximal end of the deployment system, by way of an electrically conductive graft actuator 60. Any of a wide variety of electrical conductors can be utilized for the electrically-conductive graft actuator 60, including solid wire, braided filaments and others as will be understood by those of skill in the art. In one embodiment, a solid wire having a cross section of about 0.010 inches and an insulating layer comprising polyimide and having a thickness of about 0.002 inches is utilized. The electrical conductor may contact the memory alloy wire of the graft via clasp, jaws, wire bending or intermeshing, a third segment, welds, or free contact. The electrically conductive actuator wire is preferably coated with a polymer material providing both electrical and thermal resistance. The thickness of the coating is preferably between about 0.001 inches to about 0.0015 inches. The polymer materials that can be used for the coating are materials such as PTFE, polyimide and polyester. The coating preferably provides insulation at temperatures ranging from about 20° C. to about 60° C. The electrical conductor is also retracted with the deployment system.

Figure 8:
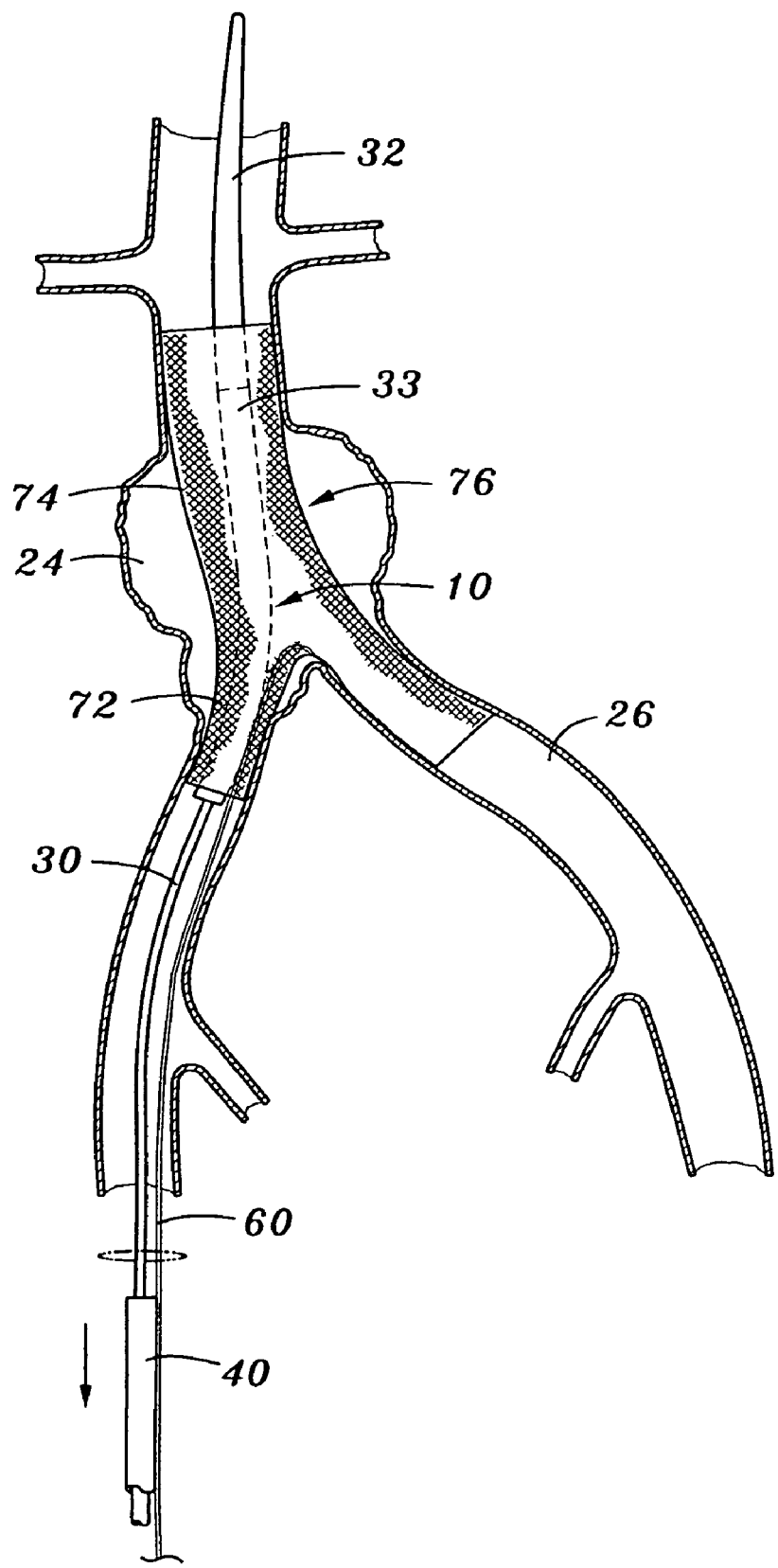
FIG. 8 is a schematic representation of the deployment system of the present invention showing withdrawal of the deployment catheter of the present invention from the fully deployed graft.
Figure 9:
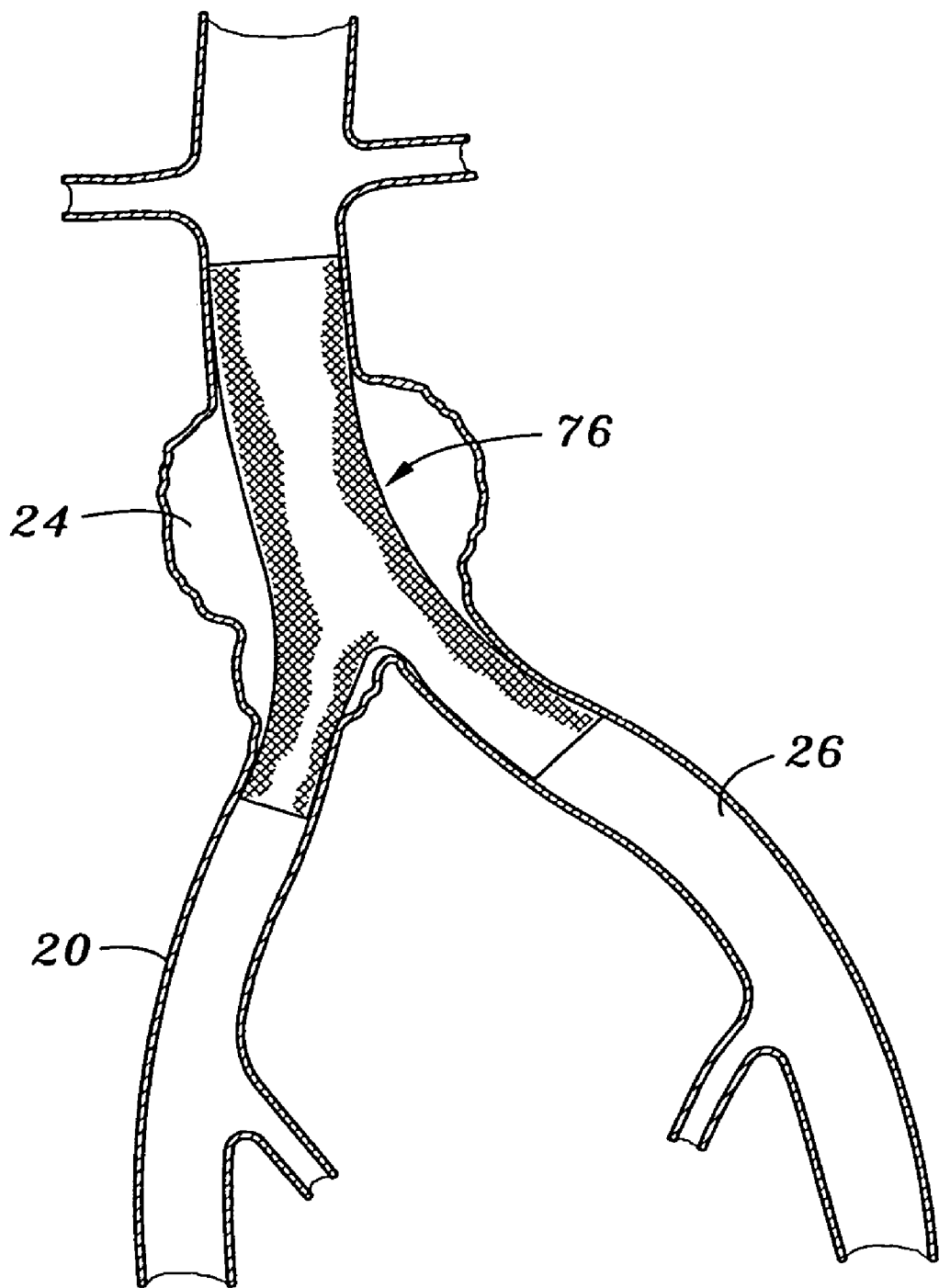
FIG. 9 is a schematic representation of the fully deployed graft of the present invention in situ.

Referring to FIG. 8, the deployment system 10, including the distal tip 32 and tubular housing 33, the inner core 30 and middle core 40, and the actuator 60, are proximally retracted through the expanded bifurcated graft 76. The deployment system may thereafter be proximally withdrawn from the patient by way of the single vascular access site, leaving only the fully deployed bifurcated graft 76 spanning the aortic aneurysm 24 as shown in FIG. 9.

Any of a variety of structures can be utilized to restrain the contralateral limb 70, during placement of the graft, and thereafter release or expand the contralateral limb 70 within the contralateral iliac. Preferably, all such restraining and release mechanisms are operated through the single vascular access site as has been discussed. Thus, in embodiments using removable mechanical retention structures such as a sheath or restraining wire proximal (inferior anatomical direction) retraction of the restraining structure will release the ipsilateral limb, whereas proximal retraction of a release wire will advance the restraining structure in the superior anatomical direction to release the contralateral limb 70. A release wire shall mean any suitable structure including a wire or cord.

Figure 10:
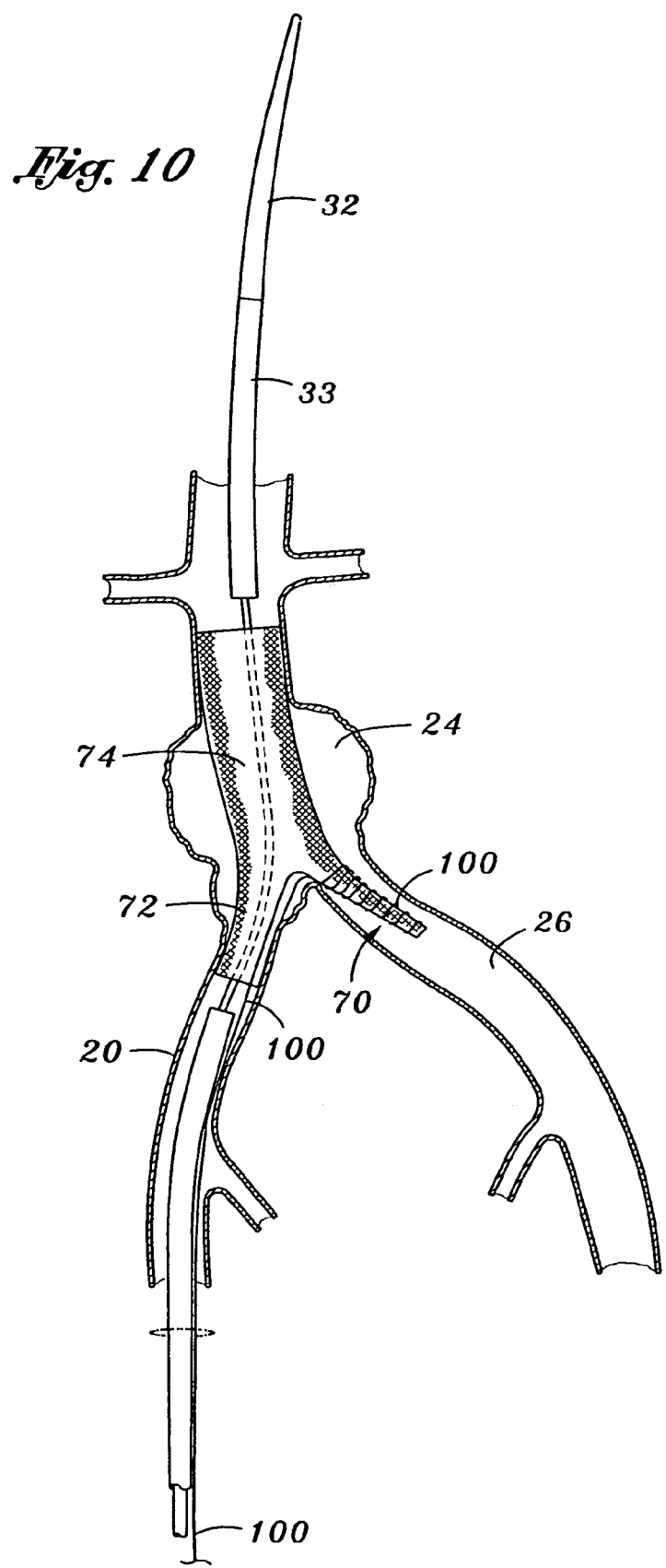
FIG. 10 is a schematic representation of a variation of the deployment system of the present invention showing retention of a self-expanding contralateral limb with a small diameter filament.

For example, a small diameter wire (e.g. 0.010 inch diameter) or low profile ribbon (e.g. 0.001 inch by 0.003 inch) restraint 100 may be wrapped or woven around a self-expanding stent cage to hold it in a collapsed profile for placement within the contralateral limb 70 as illustrated in FIG. 10. The main body 74 and ipsilateral limb 72 of the prosthesis are configured and deployed in the same manner as described previously. Following placement within the contralateral iliac as described above, the restraint 100 can be retracted from the proximal end of the deployment system, releasing the contralateral limb and allowing it to expand. The deployment system including the restraint 100 is then removed from the single access port.

Alternatively, a water soluble adhesive can be utilized to encapsulate the compressed contralateral limb 70. Following retraction of the outer sheath 50 and positioning within the contralateral iliac 26, exposure to blood causes the dissolvable restraint material to dissolve, eventually permitting the contralateral limb 70 to expand to its implanted diameter. A wide variety of biomaterials which are absorbable in an aqueous environment over different time intervals are known, including a variety of compounds in the polyglycolic acid family, as will be understood by those of skill in the art. In this embodiment, the bioadhesive or other bioabsorbable restraint compound must permit sufficient time for the contralateral limb 70 to be properly positioned within the contralateral iliac 26 before releasing the contralateral limb 70 as will be appreciated by those of skill in the art.

Figure 11:
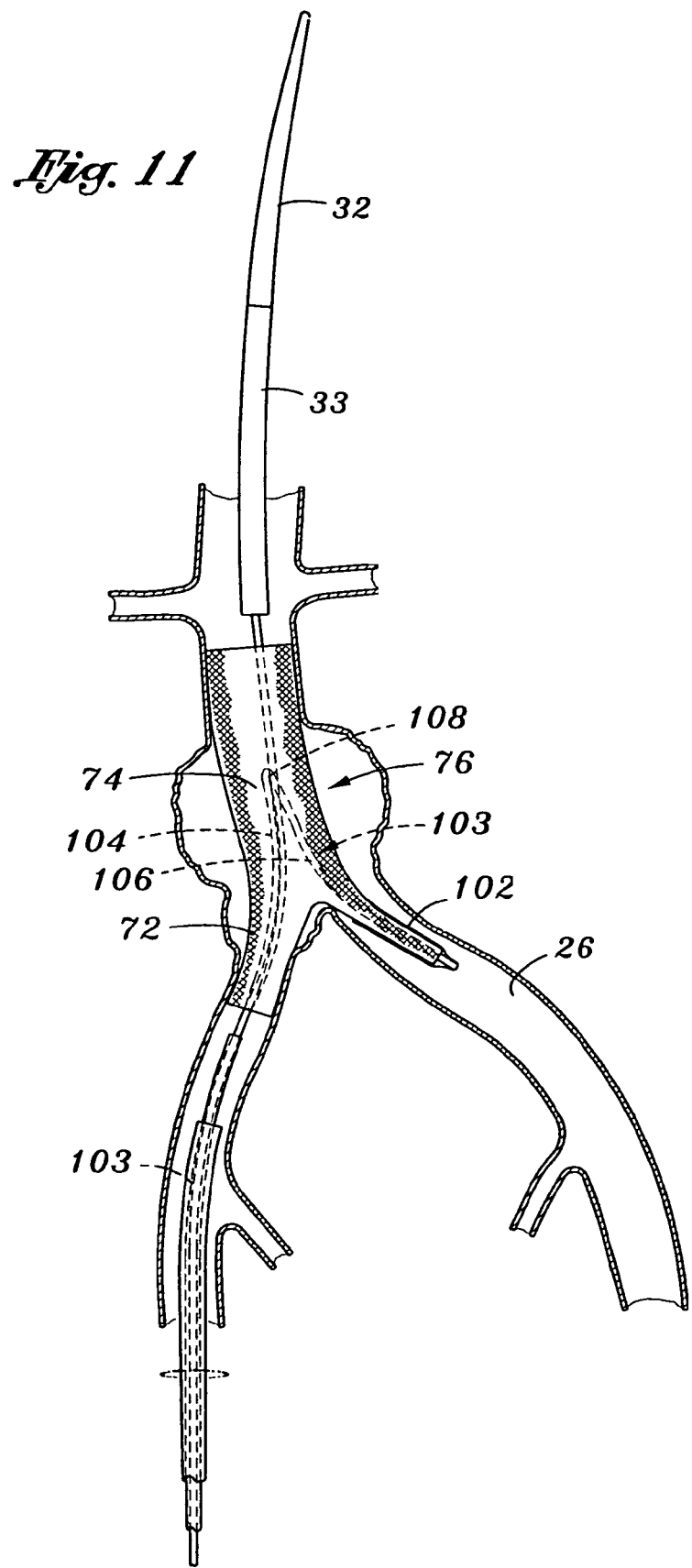
FIG. 11 is a schematic representation of another variation of the deployment system of the present invention showing a contralateral limb sheath.
Figure 12:
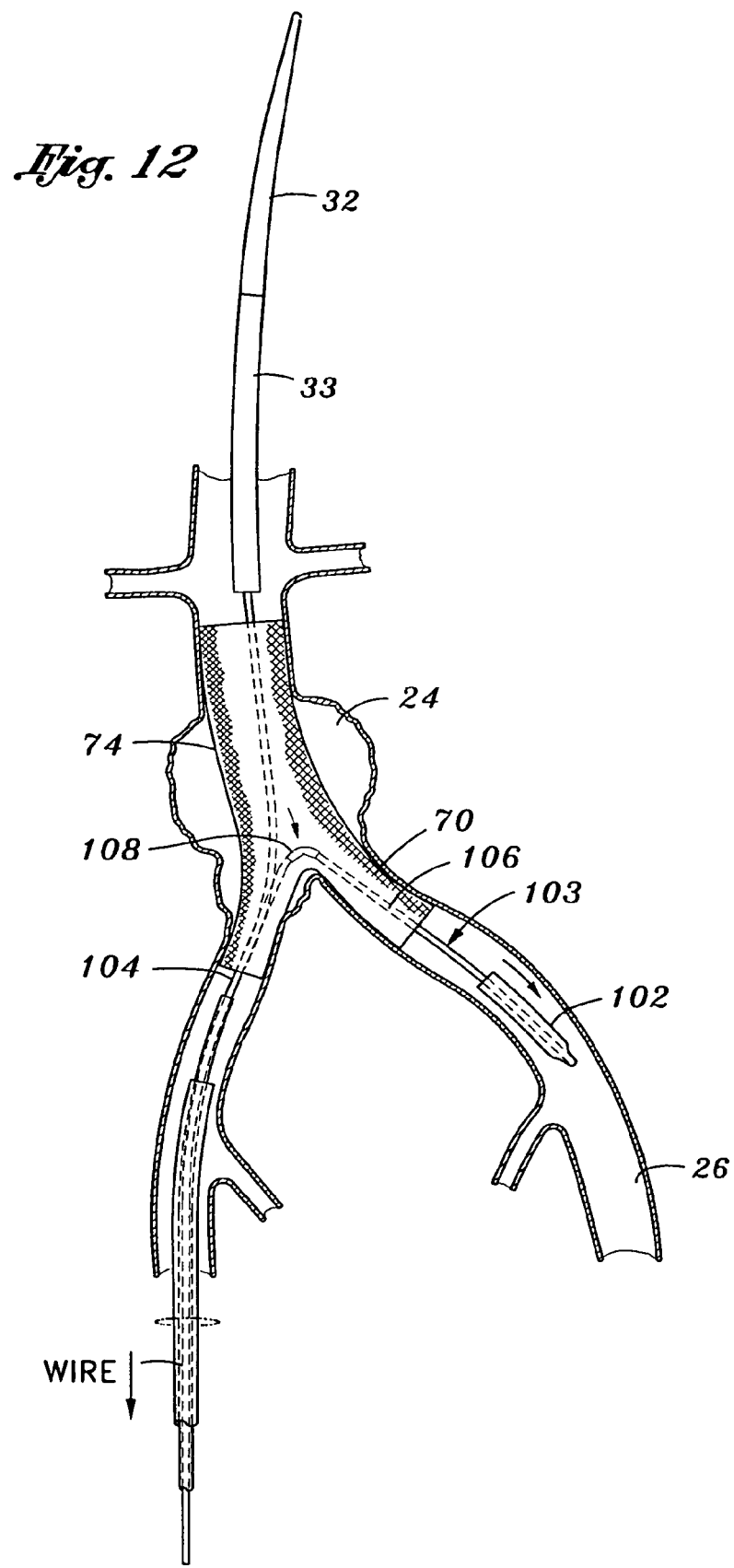
FIG. 12 is a schematic representation of the deployment system of FIG. 11, showing deployment of the contralateral limb by proximal retraction of a deployment wire.

In another variation of the single vessel deployment system of the present invention, a tubular sheath 102 is used to restrain the contralateral limb as shown in FIGS. 11 and 12. Before or after the main body 74 and ipsilateral limb 72 of the graft 76 are deployed as described above, the contralateral limb 70 is deployed by proximally retracting a release wire 103. The proximal movement of the release wire 103 causes the contralateral sheath 102 to advance inferiorly into the contralateral iliac, thereby releasing the self-expandable wire cage within the contralateral limb as depicted in FIG. 12.

In the embodiment of FIGS. 11 and 12, the release wire 103 comprises a proximal ipsilateral segment 104 and a distal, contralateral segment 106. Ipsilateral segment 104 and contralateral segment 106 are joined at an apex 108. Apex 108 may be a bend in the release wire 103, or a joint such as for securing two separate segments together. The release wire 103, particularly in the region of the apex 108, must have sufficient structural integrity that proximal retraction of the proximal end of release wire 103 will cause movement of the contralateral segment 106 in the inferior direction (down the contralateral iliac away from the aorta). The contralateral iliac segment 106 is secured at its distal end to the tubular sheath 102. The release wire 103 may be formed from any of a variety of materials and dimensions as will be apparent in view of the disclosure herein. In one embodiment a circular cross-section, solid wire having a diameter in the range of about 0.020 inches to about 0.030 inches may be used.

Following proximal retraction of the release wire 103 to deploy the contralateral iliac segment 70, the release wire 103 is advanced distally, thereby drawing the tubular sheath 102 in a superior direction through the expanded contralateral limb of the graft and towards the aorta. A medially-directed bias exerted by apex 108 urges the tubular sheath 102 in the direction of the ipsilateral iliac. Once the sheath 102 is positioned at the opening to the ipsilateral iliac, the release wire 103 may be withdrawn. Alternatively, the release wire 103 may simply be proximally withdrawn, drawing the tubular sheath 102 through the contralateral graft segment 70 as will be appreciated by those of skill in the art in view of the disclosure herein.

In a variation of this design, a wire without an apex, which is fastened to the distal tip of the sheath 102, may be retracted, thereby pulling the contralateral limb sheath from outside in, through and off of the contralateral limb and out through the lumen.

In a further embodiment of the present invention, the contralateral iliac segment 70 is restrained in its insertion profile by a peelable sheath 110. The peelable sheath 110 can be removed to release the contralateral iliac segment 70 by proximal retraction, preferably into the catheter. The use of one embodiment of a peelable sheath for restraining and deploying contralateral iliac segment 70 is illustrated in FIGS. 13 through 17.

Figure 13:
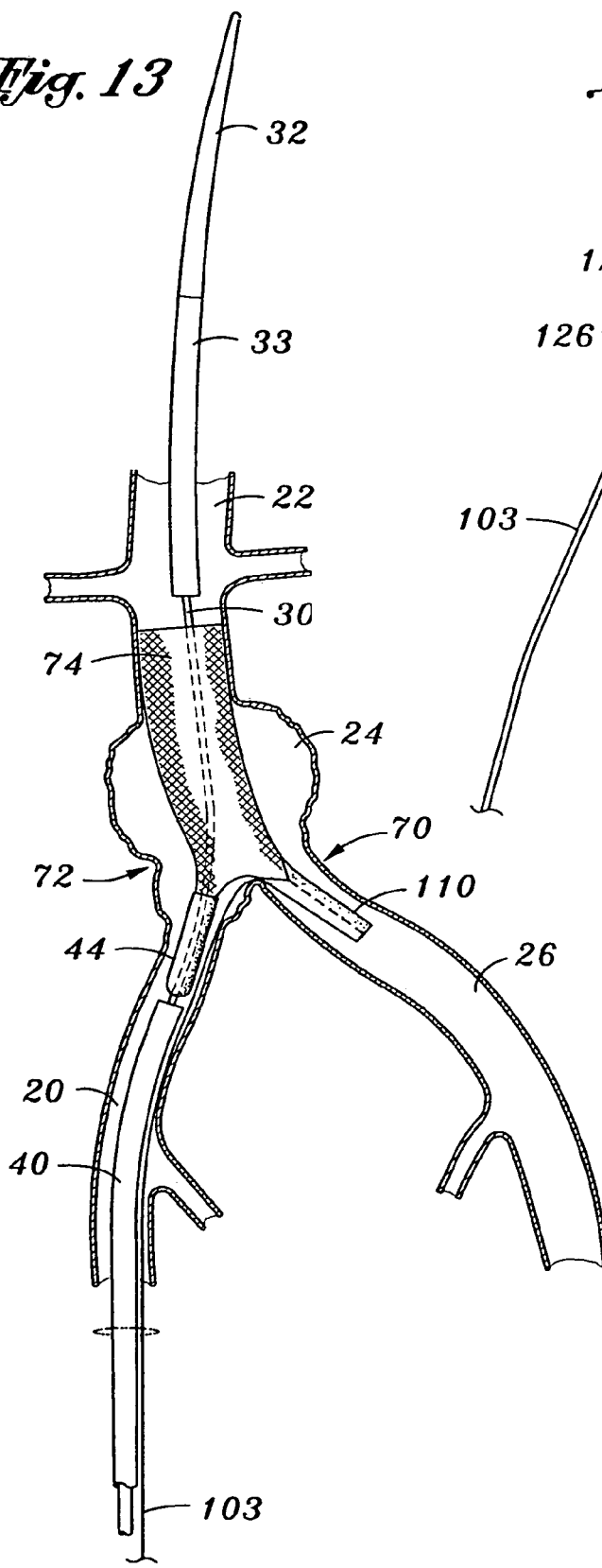
FIG. 13 is a schematic representation of a variation of the deployment system of the present invention, showing retention of the contralateral limb by a peel-away limb cover.

Referring to FIG. 13, there is illustrated a deployment device positioned within an aneurysm 24 in the aorta 22 at the bifurcation of the ipsilateral iliac 20 and contralateral iliac 26. The main body 74 of the graft has already been deployed within the aorta 22 in accordance with techniques previously disclosed.

Figure 14:
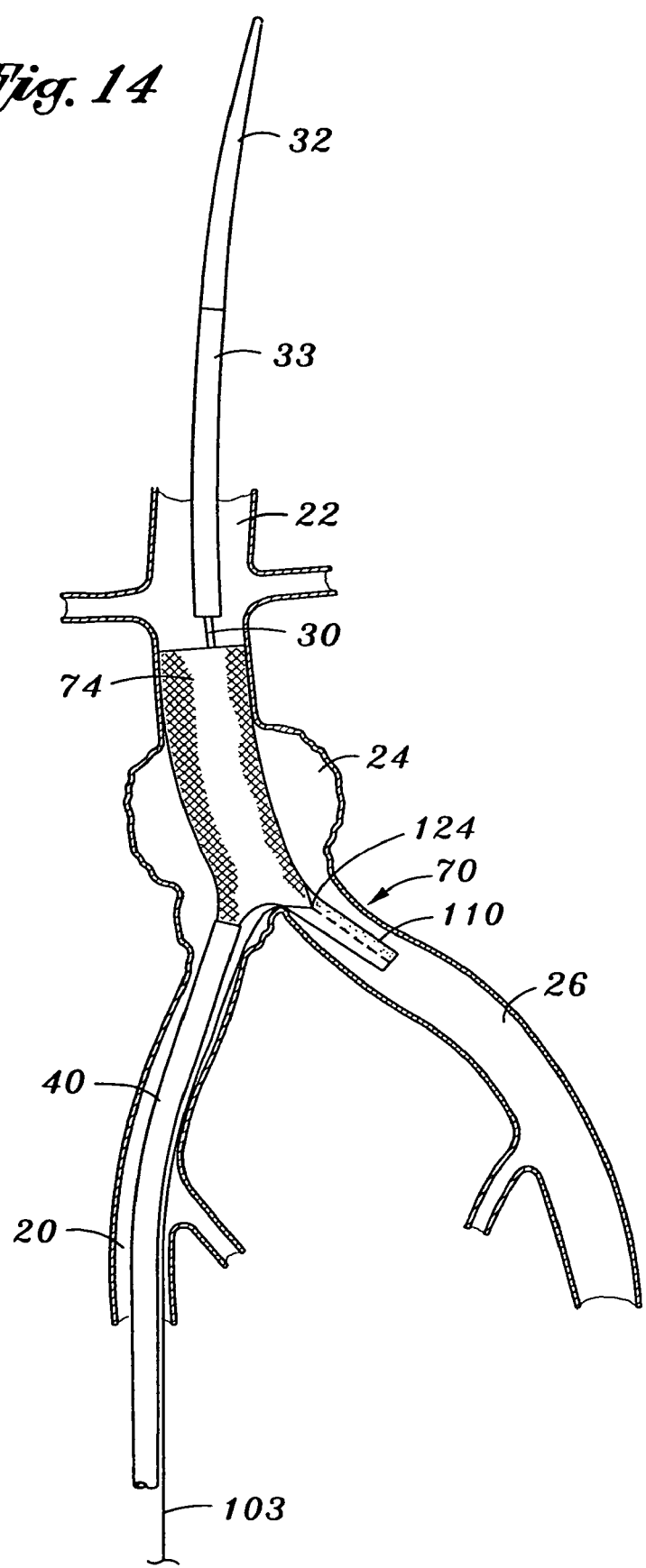
FIG. 14 is a schematic representation of the system of FIG. 13, ready for deployment of the contralateral limb.

Following retraction of the outer sheath 40 in a proximal direction to release the constrained contralateral iliac segment 70 for positioning within the contralateral iliac 26, (as illustrated in FIG. 13), the outer sheath 40 is distally advanced to the bifurcation as illustrated in FIG. 14. At this point, the system is prepared for release of the peelable sheath 110.

Figure 13A:
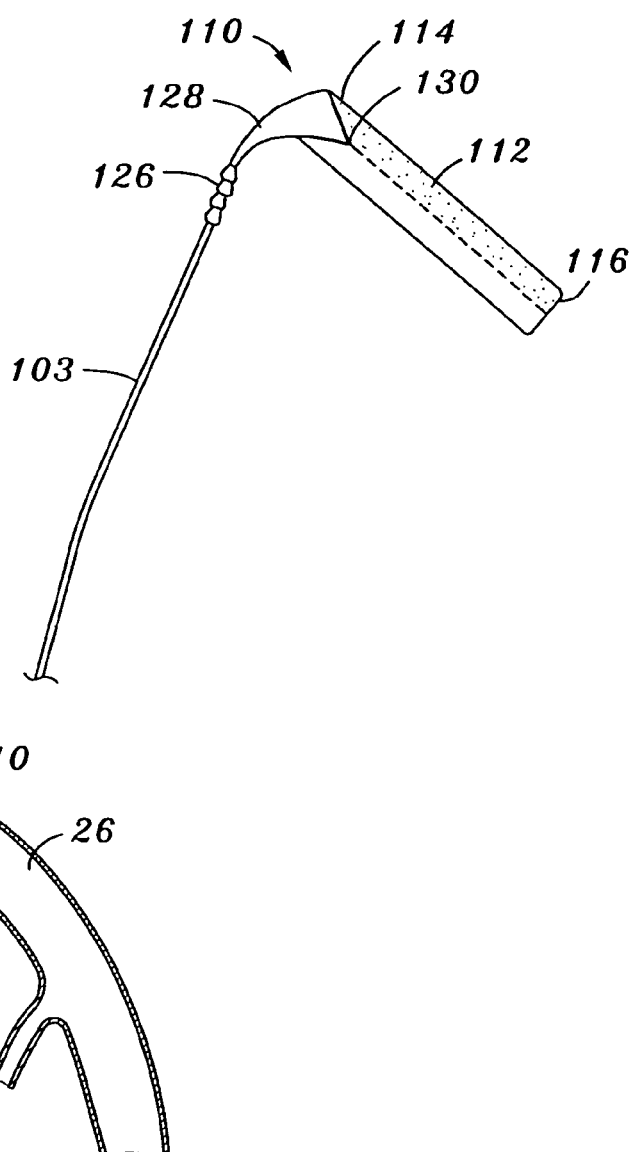
FIG. 13A is an enlarged view of a peel-away contralateral limb cover in accordance with the present invention.

Referring to FIG. 13A, a peelable sheath 110 is disclosed for releasably restraining the contralateral iliac segment 70. The peelable sheath 110 comprises a tubular body 112 having a proximal (superior) end 114 and a distal (inferior) end 116.

The peelable sheath 110 is secured to a contralateral graft actuator 60 such as a release wire 103. The release wire 103 in the illustrated embodiment is secured by way of a joint 120 to the proximal end 114 of the peelable sheath 110, and extends through the middle core 40 to the proximal end of the catheter.

The proximal end 114 of sheath 110 is preferably provided with a leader 128 of sheath material to facilitate positioning the joint 126 on the ipsilateral limb side of the bifurcation. Preferably, the peelable sheath 110 is provided with a peel start point 130 such as a slit, perforation, V-shaped cut, or otherwise as will be apparent to those of skill in the art in view of the disclosure herein. The peelable sheath 110 may further be provided with a perforation line, crease or other tear facilitating modification extending axially there along to facilitate predictable tearing of the material.

The peelable sheath 110 may be made from any of a variety of thin, tearable materials as will be apparent to those of skill in the art in view of the disclosure herein. Preferably, the material exhibits sufficient strength that it will restrain the self expandable contralateral iliac segment 70 while at the same time maintaining a low cross sectional profile and also permitting tearing to occur with a minimal amount of traction required on the release wire 103. In one embodiment, the peelable sheath 110 comprises a PTFE tube having a wall thickness of about 0.011", an outside diameter of about 0.196" and a length from the peel start point 130 to the distal end 116 of about 5.0 cm. The overall length from the joint 120 to the distal end 116 is about 6.0 cm. Specific dimensions may be optimized for any particular device as will be understood in the art. Other thin wall tearable materials may also be used, such as PET, HDPE, or PE.

Figure 15:
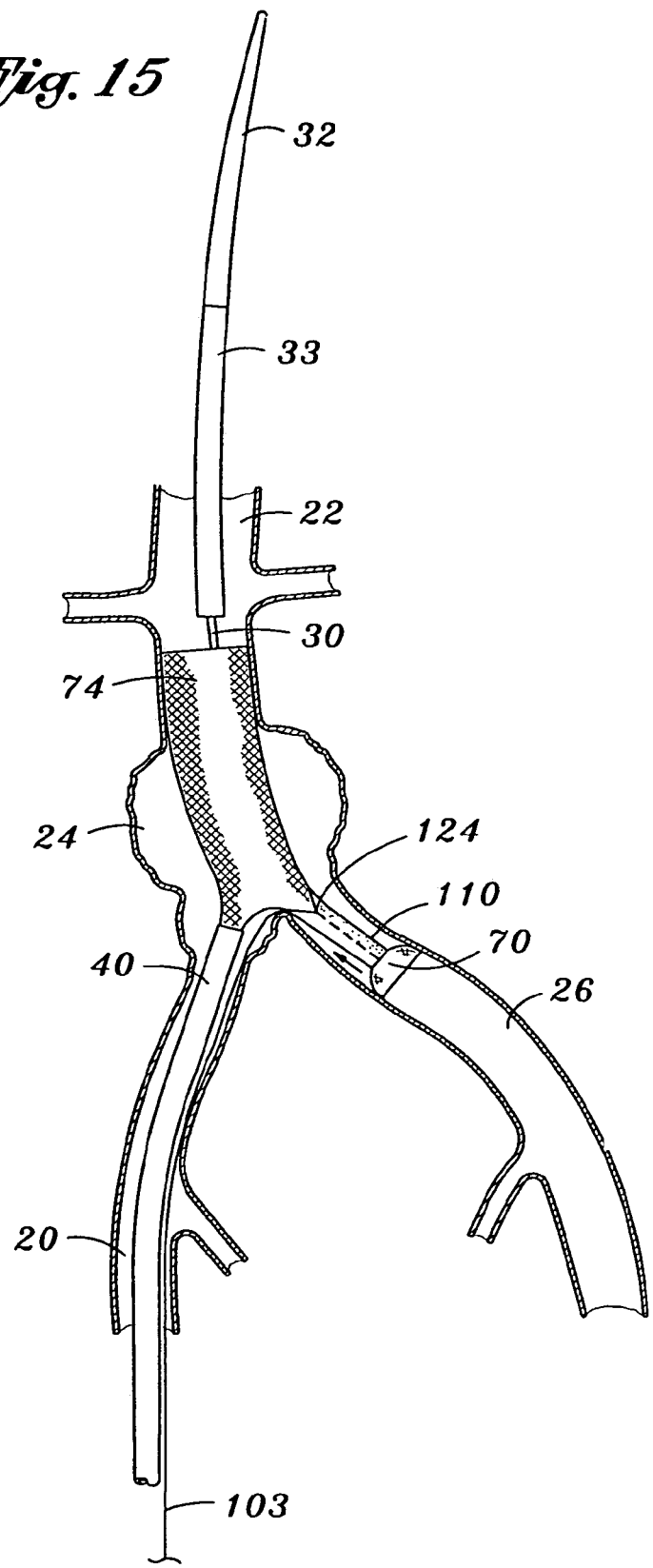
FIG. 15 is a representation of the system of FIG. 14, with the contralateral limb partially deployed.
Figure 16:
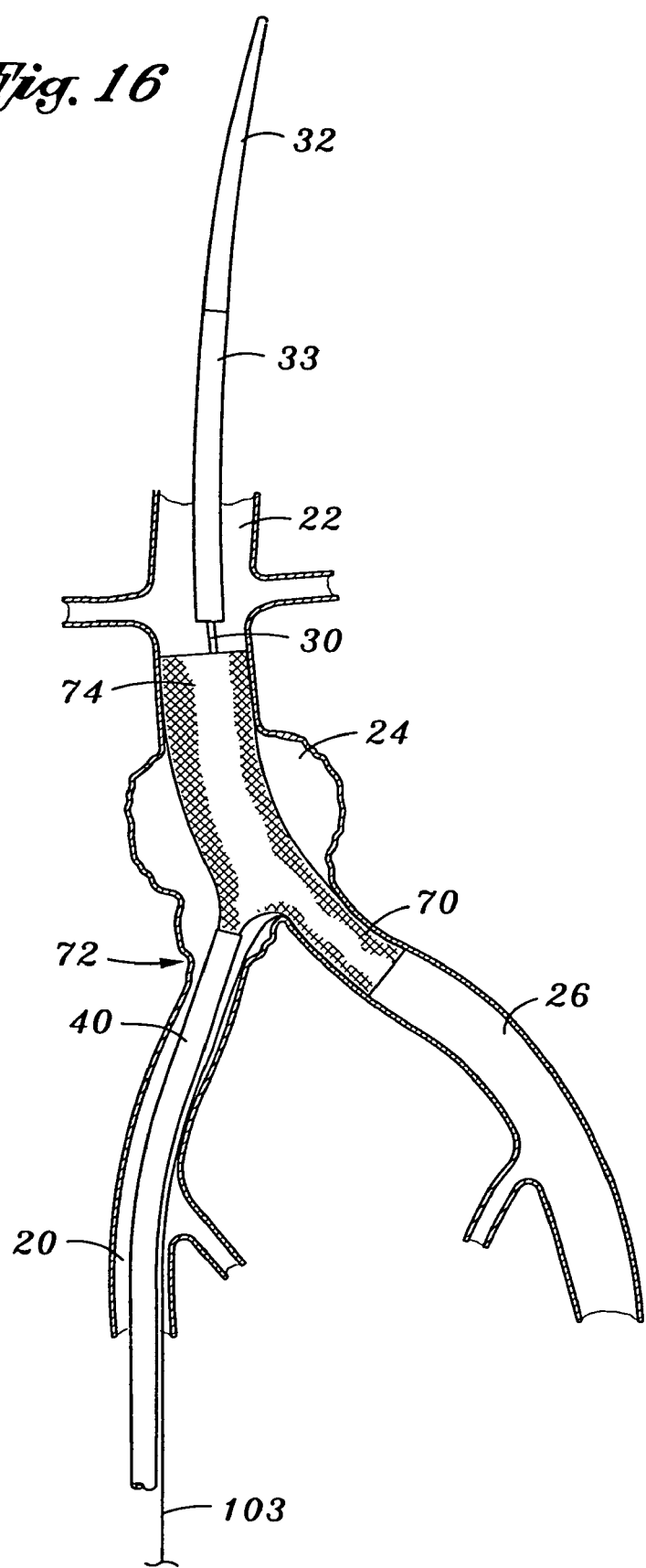
FIG. 16 is a representation as in FIG. 15, with the contralateral limb fully deployed.

Referring to FIG. 14, the distal end of the outer sheath 40 provides a fulcrum for minimizing injury to the adjacent tissue as proximal traction is applied to the release wire 103. Proximal retraction of the release wire 103 pulls the peelable sheath 110 in a proximal (superior) direction, around the bifurcation and down into the tubular outer sheath 40. As illustrated in FIG. 15, retraction of the pull wire 103 slides the tubular body 112 superiorly along the contralateral iliac segment 70 such that the contralateral iliac segment 70 is released from the inferior end first. Further proximal retraction of the release wire 103 causes the peelable sheath 110 to tear or split thereby permitting complete retraction of the peelable sheath 110 from the contralateral iliac segment 70 as illustrated in FIG. 16. Following deployment of the contralateral iliac segment 70, the middle core 40 and/or a separate ipsilateral limb cover 44, where utilized, may be proximally retracted to deploy the ipsilateral limb 72.

As will be apparent in view of the disclosure herein, the release wire 103 may extend through the outer core 50 or the middle core 40, through a dedicated lumen in the wall of either, or outside of the catheter as may be desired for particular product designs.

The release wire 103 may be attached to the peelable sheath 110 at either the proximal end 1.14 or the distal end 116. In the illustrated embodiment, the release wire 103 is attached to the leader 128 at joint 126. Joint 126 comprises a barbed metal cylinder for grabbing the PTFE. Any of a variety of alternate structures or materials for fastening the release wire 103 to the peelable sheath 110 may alternatively be utilized provided the joint 126 has sufficient integrity to pull the peelable sheath 110 and permit splitting of the sheath to release the contralateral iliac segment 170.

Although the peelable sheath 110 in the foregoing embodiment was disclosed as restraining the contralateral iliac limb, the peelable sheath may be used on any of the contralateral, ipsilateral, or main branch portions of the graft. For example, in one embodiment, the main body portion of the graft is restrained within the graft tube 33, and each of the contralateral and ipsilateral iliac graft branches are restrained by a peelable sheath. In an alternate embodiment, all three portions of the graft are restrained by peelable sheaths. As a further alternative, the main graft body and the contralateral iliac limb portions of the graft are restrained by first and second peelable sheaths and the ipsilateral portion of the graft is restrained by a proximally retractable sleeve as has been disclosed previously herein. The desirability of any of the foregoing combinations will be apparent to one of ordinary skill in the art in view of the design parameters for a particular catheter built in accordance with the present invention.

Referring to FIG. 18, an embodiment of a self-expanding bifurcated prosthesis in accordance with the present invention is shown having a polymeric sleeve 80 and a tubular wire support 90. Many of the features of the self-expandable graft of the present invention are disclosed in co-pending U.S. patent application Ser. No. 09/100,481 entitled "Self Expanding Bifurcated Endovascular Prosthesis," filed Jun. 19, 1998, and copending U.S. patent application Ser. No. 09/210,280, entitled "Endoluminal Vascular Prosthesis," filed Dec. 11, 1998, the disclosures of which are incorporated in their entirety herein by reference.

The polymeric sleeve 80 may be situated concentrically outside of the tubular wire support 90. However, other embodiments may include a sleeve situated instead concentrically inside the wire support or on both of the inside and the outside of the wire support. Alternatively, the wire support may be embedded within a polymeric matrix that makes up the sleeve. Regardless of whether the sleeve is inside or outside the wire support, the sleeve may be attached to the wire support by any of a variety of means, including laser bonding, adhesives, clips, sutures, dipping or spraying or others, depending upon the composition of the sleeve and overall graft design.

The polymeric sleeve may be formed from any of a variety of synthetic polymeric materials, or combinations thereof, including PTFE, PE, PET, Urethane, Dacron, nylon, polyester or woven textiles. Preferably, the sleeve material exhibits relatively low inherent elasticity, or low elasticity out to the intended enlarged diameter of the wire cage. The sleeve material preferably has a thin profile, such as no larger than about 0.002 inches to about 0.005 inches.

In one embodiment of the invention, the material of the sleeve is sufficiently porous to permit in-growth of endothelial cells, thereby providing more secure anchorage of the prosthesis and potentially reducing flow resistance, shear forces, and leakage of blood around the prosthesis. Porosity in polymeric sleeve materials may be estimated by measuring water permeability as a function of hydrostatic pressure, which will preferably range from about 3 to 6 psi.

The porosity characteristics of the polymeric sleeve may be either homogeneous throughout the axial length of the prosthesis, or may vary according to the axial position along the prosthesis. For example, at least a distal portion and right and left proximal portions of the prosthesis will seat against the native vessel walls, proximally and distally of the aneurysm. In at least these proximal and distal portions, the prosthesis preferably encourages endothelial growth, or, at least, permits endothelial growth to infiltrate portions of the prosthesis in order to enhance anchoring and minimize leakage. For the central portion of the prosthesis, which spans the aneurysm, anchoring is less of an issue. Instead, minimizing blood flow through the prosthesis wall becomes a primary objective. Thus, in a central zone of the prosthesis, the polymeric sleeve may either be nonporous; or provided with pores that minimize or prevent leakage.

A multi-zoned prosthesis may also be provided in accordance with the present invention by positioning a tubular sleeve on a central portion of the prosthesis, such that it spans the aneurysm to be treated, but leaving the wire support in the proximal and distal attachment zones exposed. In this embodiment, the exposed wires are positioned in contact with the vessel wall both proximally and distally of the aneurysm, such that the wire, over time, becomes embedded in cell growth on the interior surface of the vessel wall.

In one embodiment of the prosthesis, the sleeve and/or the wire support is stepped or tapered, having a relatively larger expanded diameter at the proximal end compared to the distal ends. The tapered design may allow the prosthesis to conform better to the natural decreasing distal cross section of the aorta and iliac arteries to reduce the risk of leakage and graft migration and potentially create better flow dynamics.

Referring to FIG. 18, the tubular wire support comprises a main body 92 for traversing the aorta and a first, ipsilateral iliac limb 94, and a secondary component for extending into the second, contralateral iliac limb 96. The contralateral limb cage may be constructed from a memory alloy wire such as Nitinol as has been discussed. The main body and ipsilateral limb structures may be constructed from a non-memory alloy wire.

Referring to FIG. 19, one embodiment of the prosthesis 76 is shown, wherein the limbs expand laterally away from one another due to an expansion spring 120, comprising an apex and first and second leg portions. The leg portions are connected to the wire cage 90 of both the ipsilateral and contralateral limbs at connection point 122. The apex 124 of the expansion spring 120 is located at the bifurcation.

With reference to FIG. 20, one embodiment of the wire structure for the primary wire support components is shown, wherein the wire cage is formed from one or more lengths of wire into a series of straight struts separated by apexes into a zig-zag pattern. The contralateral wire cage may also be constructed from one or more zig-zag wires as illustrated. When a tubular wire cage is formed by rolling the formed wire about an axis, the connectors 98 collectively produce a generally axially extending backbone that adds axial strength to the prosthesis. The wire support is formed in a plurality of discrete segments, connected together and oriented about a common axis. A connector wire 98 connects adjacent segments together. Opposing wire apexes of adjacent segments can be connected in any of a variety of ways including circumferentially extending sutures, solder joints, wire loops and any of a variety of interlocking relationships, such as those disclosed in copending U.S. patent application Ser. No. 09/210,280, filed Dec. 11, 1998, entitled "Endoluminal Vascular Prosthesis", the disclosure of which is incorporated in its entirety herein by reference. The contralateral limb cage may be joined to the main body and ipsilateral limb component by similar sutures, solder joints, wire loops and/or interlocking relationships.

The segmented configuration of the tubular wire supports facilitates a great deal of flexibility. Each segment, though joined to adjacent segments, may be independently engineered to yield desired parameters. Each segment may range in axial length from about 0.3 to about 5 cm. Generally, the shorter their length the greater the radial strength. The primary component of an endoluminal prosthesis may include from about 2 to about 50 segments, preferably from about 8 to about 16 segments.

In general, each of the components of the tubular wire support can be varied considerably in diameter, length, and expansion coefficient, depending upon the intended application. For implantation within a typical adult, the aorta trunk portion will have a length within the range of from about 5 cm to about 12 cm, and, typically within the range of from about 9 cm to about 10 cm. The unconstrained outside expanded diameter this portion will typically be within the range of from about 20 mm to about 40 mm. The unconstrained expanded outside diameter of this portion can be constant or substantially constant throughout its length, or can be tapered from a relatively larger diameter at the proximal end to a relatively smaller diameter at the bifurcation. In general, the diameter of the distal end will be on the order of no more than about 95% and, preferably, no more than about 85% of the diameter of the proximal end of the aortic trunk portion.

Different zones of the prosthesis can be provided with differing expanded diameters. Further, the different zones can be provided with a different radial expansion force, such as ranging from about 2 lbs. to about 8 lbs. In one embodiment, the proximal zone is provided with a greater radial force than the central zone and/or distal zone. A greater radial force can be provided in any of a variety of manners, such as through the use of additional wire bends and wall sections. Alternatively, additional spring force can be achieved through the use of a heavier gauge wire. Increased radial force and expansion diameter in the proximal and distal regions relative to a central region can be achieved by tightening a circumferential suture such that the central region is retained under compression even in the expanded configuration. By omitting a circumferential suture at the proximal end and/or distal ends of the prosthesis, the proximal end and distal ends will flair radially outwardly to a fully expanded configuration.

The wire for the main body and ipsilateral limb cages may be made from any of a variety of different alloys, such as elgiloy or MP35N, or other alloys which include nickel, titanium, tantalum, or stainless steel, high Co—Cr alloys or other temperature sensitive materials. For example, an alloy comprising Ni 15%, Co 40%, Cr 20%, Mo 7% and balance Fe may be used. The tensile strength of suitable wire is generally above about 300 K psi and often between about 300 and about 340 K psi for many embodiments. In one embodiment, a Chromium-Nickel-Molybdenum alloy such as that marketed under the name Conichrom (Fort Wayne Metals, Indiana) has a tensile strength ranging from 300 to 320 K psi, elongation of 3.5-4.0% and breaking load at approximately 80 lbs. to 70 lbs. As mentioned above, at least the contralateral limb cage may be constructed from a memory alloy such as Nitinol, which will remain in a small profile until heated to the memory alloy's transition temperature, at which point the contralateral limb cage expands to a predisposed shape. In any case, both the memory and non-memory alloy wires may be treated with a plasma coating and be provided with or without additional coatings such as PTFE, Teflon, Perlyne, drugs, and others as will be understood by those of skill in the art.

In addition to segment length and bend configuration, another determinant of radial strength is wire gauge. The radial strength, measured at 50% of the collapsed profile, preferably ranges from about 2 lb. to 8 lb., and generally from about 4 lb. to about 5 lb. or more. Preferred wire diameters in accordance with the present invention range from about 0.004 inches to about 0.020 inches. More preferably, the wire diameters range from about 0.006 inches to about 0.018 inches. In general, the greater the wire diameter, the greater the radial strength for a given wire layout. Thus, the wire gauge can be varied depending upon the application of the finished graft, in combination with/or separate from variation in other design parameters.

A wire diameter of approximately 0.018 inches may be useful in the aorta trunk portion of a graft, while a smaller diameter such as 0.006 inches might be useful for the iliac limb segment.

In one embodiment of the present invention, the wire diameter is tapered throughout from the proximal to distal ends. Alternatively, the wire diameter may be tapered incremental or stepped down, or stepped up, depending on the radial strength requirements of each particular clinical application. In general, in the tapered or stepped wire embodiments, the diameter of the wire in the iliac branches is no more than about 80%, preferably no more than about 50%, and optimally no more than about 35% of the diameter of the wire in the aortic trunk. This permits increased flexibility of the graft in the region of the iliac branches, which has been determined by the present inventors to be clinically desirable.

Additional details of the wire cage layout and construction can be found in co-pending U.S. patent application Ser. No. 09/034,689 entitled "Endoluminal Vascular Prosthesis," filed Mar. 4, 1998, the disclosure of which is incorporated in its entirety herein by reference.

The collapsed prosthesis in accordance with the present invention has a diameter in the range of about 2 to about 10 mm. Preferably, the maximum diameter of the collapsed prosthesis is in the range of about 3 to 6 mm (12 to 18 French). More particularly, the delivery catheter including the prosthesis will be 19 F, 16 F, 14 F, or smaller. After deployment, the expanded endoluminal vascular prosthesis radially self-expands to a diameter anywhere in the range of from about 20 to about 40 mm, corresponding to expansion ratios of about 1:2 to 1:20. In a preferred embodiment, the expansion ratios range from about 1:4 to 1:8, more preferably from about 1:4 to 1:6.

While a number of variations of the invention have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A method of transluminally deploying a bifurcation graft at the bifurcation of a main vessel into a first and second branch vessels, comprising:
   providing a bifurcation graft having a main portion, a first branch portion, and a second branch portion, the bifurcation graft supported by a single delivery catheter with the main portion, the first branch and the second branch portion constrained in a radially compressed state by one or, the main portion having a diameter greater than a diameter of the first branch portion or the second branch portion;
   introducing distally the delivery catheter and the bifurcation graft through a first access site in the first or second branch vessel;
   transluminally advancing the bifurcation graft to the bifurcation;
   manipulating the delivery catheter to position the bifurcation graft such that the main portion is in the main vessel, the first branch portion is positioned at least partially in the first branch vessel, and the second branch portion is positioned at least partially in the second branch vessel;
   proximally retracting the bifurcation graft until the bifurcation of the graft is positioned in contact with the bifurcation between the first and second branch vessels, wherein the bifurcation of the graft is the juncture of the first branch portion and the second branch portion;
   expanding the main, first branch and second branch portions from their radially compressed states; and
   withdrawing the delivery catheter and each of the one or more restraints through the first access site;
   wherein the bifurcation prevents distal migration of the bifurcation graft.

2. The method of claim 1, wherein the main vessel is the aorta artery, the first branch vessel is the ipsilateral iliac artery and the second branch vessel is the contralateral iliac artery.

3. The method of claim 1, wherein the step of proximally retracting the bifurcation graft until the bifurcation of the graft is positioned on the bifurcation between the first and second branch vessels comprises positioning the second branch portion on the bifurcation between the first and second branch vessels.

4. The method of claim 3, wherein the bifurcation graft is introduced through the first access site and into the first branch vessel.

5. The method of claim 1, wherein the step of expanding the main, first branch and second branch portions from their radially compressed states comprises expanding the main portion before the first and second branch portions.

6. The method of claim 1, wherein the step of expanding the first branch portion is accomplished by removing a tubular restraining sheath from around the first branch portion.

7. The method of claim 6, wherein the removing step comprises axially displacing the restraining sheath from the first branch portion.

8. The method of claim 1, wherein the second branch portion comprises a wire support formed from a memory metal alloy.

9. The method of claim 8, wherein the second branch portion is expanded by heating the wire support.

10. The method of claim 1, wherein the second branch portion comprises a peelable sheath.

11. The method of claim 1, wherein the step of expanding the second branch portion is accomplished by removing a peelable sheath from the second branch portion.

12. The method of claim 11, wherein the peelable sheath is removed by proximally retracting a release wire.

13. The method of claim 1, wherein the second branch portion comprises a self-expandable wire support.

14. The method of claim 13, wherein the second branch portion is restrained in a radially compressed state by a biodegradable adhesive.

15. The method of claim 1, wherein the step of expanding the second branch portion is accomplished by removing a restraining sheath from around the second branch portion.

16. The method of claim 15, wherein the restraining sheath is tubular.

17. The method of claim 15, wherein the restraining sheath is removed by distally advancing the restraining sheath.

18. The method of claim 15, wherein the removing step comprises tearing the restraining sheath.

19. The method of claim 15, wherein the removing step comprises axially displacing the restraining sheath relative to the second branch portion.

20. The method of claim 1, wherein the step of expanding the second branch portion is accomplished by applying an electrical current thereto.

21. The method of claim 1, wherein the second branch portion is expanded from its radially compressed state by axially displacing an elongate release element attached to a second branch portion restraint.

* * * * *